(12) United States Patent
Barkol et al.

(10) Patent No.: US 12,254,965 B2
(45) Date of Patent: Mar. 18, 2025

(54) DEVICES AND METHOD FOR A HEALTHCARE COLLABORATION SPACE

(71) Applicant: General Electric Company, Schenectady, NY (US)

(72) Inventors: Omer Barkol, Haifa (IL); Sagi Schein, Kiryat Tivon (IL); Ruth Bergman, Haifa (IL); Paul Mullen, Waukesha, WI (US); Ludovic Avot, Croissy sur Seine (FR); Jeffrey Hersh, Hopkinton, MA (US)

(73) Assignee: General Electric Company, Schenectady, NY (US)

( * ) Notice: Subject to any disclaimer, the term of this patent is extended or adjusted under 35 U.S.C. 154(b) by 637 days.

(21) Appl. No.: 17/514,826

(22) Filed: Oct. 29, 2021

(65) Prior Publication Data

US 2022/0051770 A1    Feb. 17, 2022

Related U.S. Application Data

(63) Continuation of application No. 15/984,172, filed on May 18, 2018, now Pat. No. 11,170,881.

(51) Int. Cl.
*G16H 10/60*      (2018.01)
*G06F 3/0482*    (2013.01)
(Continued)

(52) U.S. Cl.
CPC .......... *G16H 10/60* (2018.01); *G06F 3/0482* (2013.01); *G06F 3/0484* (2013.01); *G06F 3/167* (2013.01); *G08B 21/02* (2013.01); *H04L 51/216* (2022.05)

(58) Field of Classification Search
None
See application file for complete search history.

(56) References Cited

U.S. PATENT DOCUMENTS

| 2014/0249831 | A1 | 9/2014 | Gallopyn |
| 2017/0140105 | A1 | 5/2017 | Smith |
| 2018/0277246 | A1* | 9/2018 | Zhong ................... A61B 5/746 |

OTHER PUBLICATIONS

Shashikumar SP, Stanley MD, Sadiq I, Li Q, Holder A, Clifford GD, Nemati S. Early sepsis detection in critical care patients using multiscale blood pressure and heart rate dynamics. J Electrocardiol. Nov.-Dec. 2017;50(6):739-743. doi: 10.1016/j.jelectrocard.2017.08.013. Epub Aug. 16, 2017. (Year: 2017).*

(Continued)

*Primary Examiner* — Devin C Hein

(57) ABSTRACT

Various systems and devices are provided for facilitating communication in a healthcare setting. In one example, a system for providing medical information can include a processor that, in response to executing machine-readable instructions, can generate a patient dashboard comprising the medical information for a patient and a patient communication thread. The processor can also output the patient dashboard to a display, wherein the patient dashboard further comprises a first link proximate to a displayed parameter from the medical information and the processor can obtain communication among care providers monitoring the patient and virtual healthcare assistants configured to communicate on the communication thread. The processor can also output the communication from the care providers, the virtual healthcare assistances, or any combination thereof, in the patient communication thread of the patient dashboard provided by the display.

20 Claims, 10 Drawing Sheets

(51) Int. Cl.
   *G06F 3/0484*     (2022.01)
   *G06F 3/16*       (2006.01)
   *G08B 21/02*      (2006.01)
   *H04L 51/216*     (2022.01)

(56) References Cited

OTHER PUBLICATIONS

CN application 201980026956.X filed Oct. 20, 2020—Office Action issued Jan. 30, 2024, 10 pages.

* cited by examiner

DEVICES AND METHOD FOR A HEALTHCARE COLLABORATION SPACE

CROSS-REFERENCE TO RELATED APPLICATIONS

The present matter is a continuation of and claims priority to U.S. patent application Ser. No. 15/984,172, filed May 18, 2018, and titled "DEVICES AND METHOD FOR A HEALTHCARE COLLABORATION SPACE," the contents of which are incorporated herein by reference.

FIELD

Embodiments of the subject matter disclosed herein relate to healthcare communication, and in particular to healthcare communication in an acute care environment.

BACKGROUND

Acute or sub-acute care of patients in a hospital or other medical facility may be carried out with multiple care providers per patient and may include multiple patient monitoring devices monitoring each patient. Thus, to ensure a rapid response should a patient's condition deteriorate, near-continuous monitoring of the output from the multiple monitoring devices may be necessary. Further, coordination of patient care among all the care providers may be complicated or time-consuming, further stretching care provider resources.

BRIEF DESCRIPTION

In one embodiment, a system includes a display and a computing device operably coupled to the display. The computing device stores instructions executable to output, to the display, a patient-specific dashboard including medical information specific to the patient, the dashboard further including a displayed link to a patient-specific communication thread; and responsive to a user selecting the link, output to the display a portion of the communication thread, where the communication thread includes communication among one or more care providers monitoring the patient and one or more virtual healthcare assistants.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
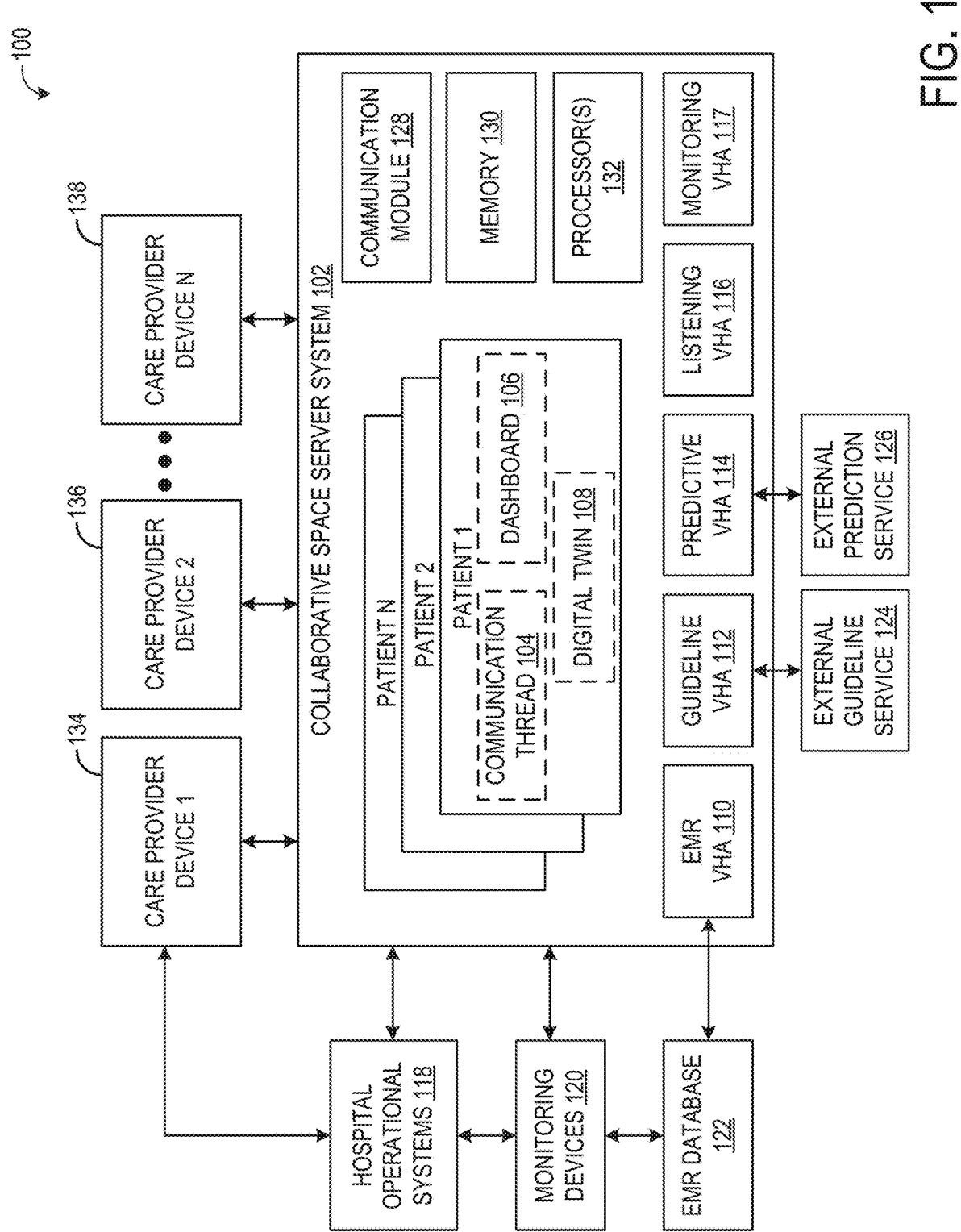
FIG. 1 schematically shows an example collaborative healthcare system.

The following description relates to various embodiments of a collaborative healthcare system that facilitates communication among care providers of a patient and also utilizes virtual healthcare assistants to perform certain patient monitoring activities. The collaborative healthcare system includes patient-specific communication channels that include communication thread-dashboard pairs to facilitate communication among the care providers and virtual healthcare assistants (also referred to as bots) on the communication thread while also graphically providing relevant patient care information (current vital signs, trends, medical history) to the care providers via the dashboard.

The virtual healthcare assistants may function as information retrievers, data monitors, predictors, and more to assist the care providers. The virtual healthcare assistants may provide requested patient data (e.g., fetch data from an electronic medical record), detect changes in patient state and alert the care providers of the changed state (e.g., by detecting that a patient vital sign has reached a condition relative to a threshold), and provide care guidelines and diagnoses to the care providers. The virtual healthcare assistants may be trained to communicate using natural language including medical language, thereby allowing for care providers to communicate with the virtual healthcare assistants in the same manner as other care providers.

Each communication channel may be specific to a given patient in a given acute care facility or other medical facility or healthcare setting (e.g., hospital, urgent care facility, or nursing home). A communication channel may be initiated upon admission of the patient to the medical facility. Each care provider of the patient may be joined to the communication channel, thereby allowing collaboration and communication among all care providers (e.g., doctors, nurses, and/or specialists such as radiologists) of the patient. The one or more virtual healthcare assistants may also be joined to the communication channel. Communication occurring on the communication channel may be in the form of text messages, rich media, and/or other forms, thereby allowing care providers to view graphs of patient medical trends, medical images, and so forth. Messages sent and received on the communication channel may be saved at a central location as a communication thread, allowing care providers to access prior conversations on the channel. For example, if a virtual healthcare assistant detects a change in a patient condition that indicates potential health issues, such as high blood pressure, the virtual healthcare assistant may note the high blood pressure and alert the care provider(s) via the communication thread. The blood pressure may be displayed via the patient dashboard along with the alert. A care provider may view the blood pressure measurement by selecting the alert in the communication thread. Later, the care provider may select a graphical display of the alert in the dashboard in order to launch the portion of the communication thread in which the blood pressure alert was issued.

The dashboard and communication thread may be viewable from a variety of client devices, including but not limited to a provider client device (such as a monitor in a nurse's station) and a provider mobile device (such as a tablet or smart phone). Thus, care providers may have access to relevant data and assistance from the virtual healthcare assistants from virtually any allowed location within the medical facility, and even off-site locations in some examples.

Figure 2:
FIG. 2 shows an example display device displaying a communication thread occurring on a communication channel of the collaborative healthcare system.
Figure 3:
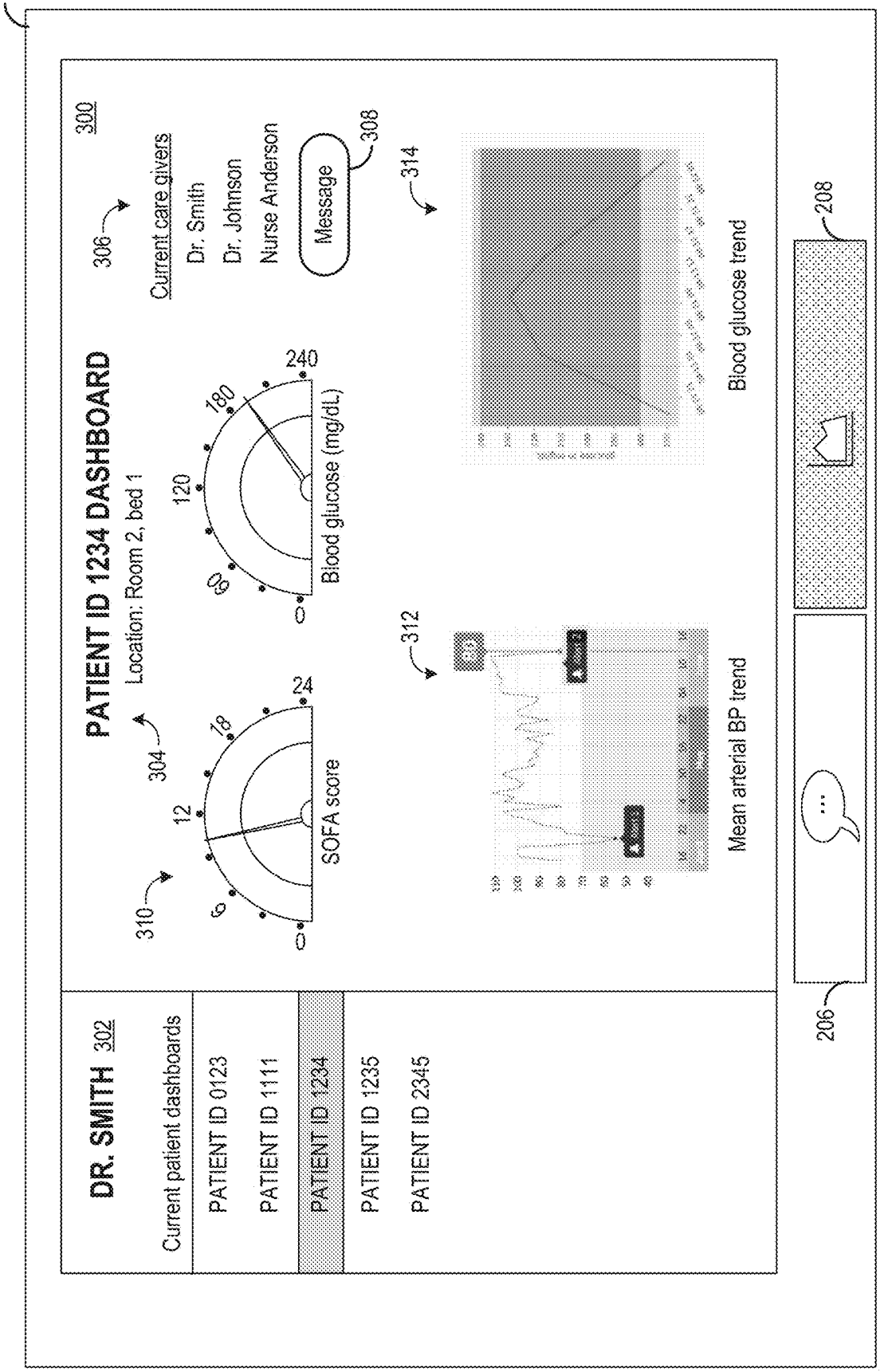
FIG. 3 shows an example display device displaying a dashboard of the collaborative healthcare system.
Figure 4:
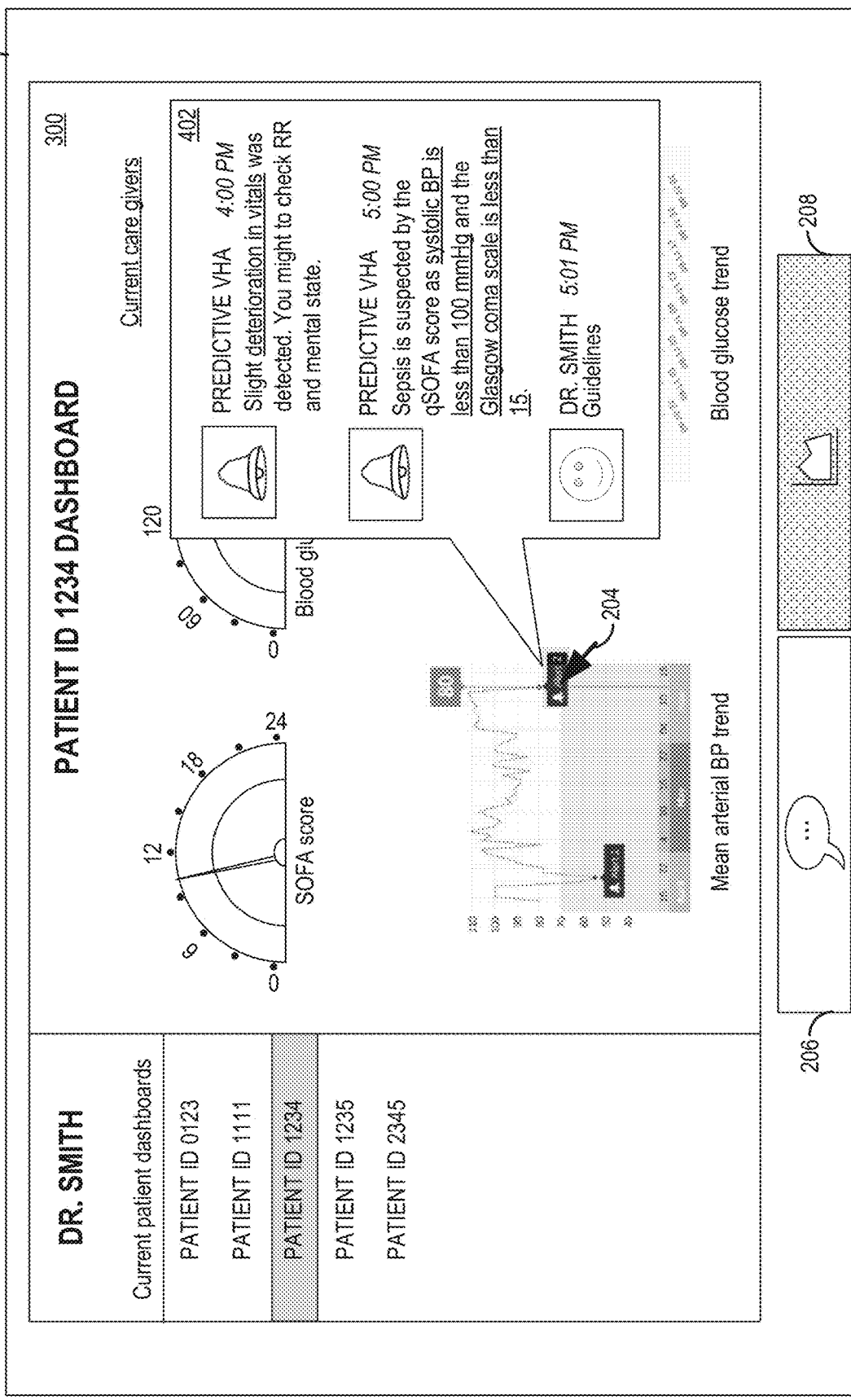
FIG. 4 shows an example display device displaying the dashboard of FIG. 3 including display of a portion of the communication thread of FIG. 2.
Figure 5:
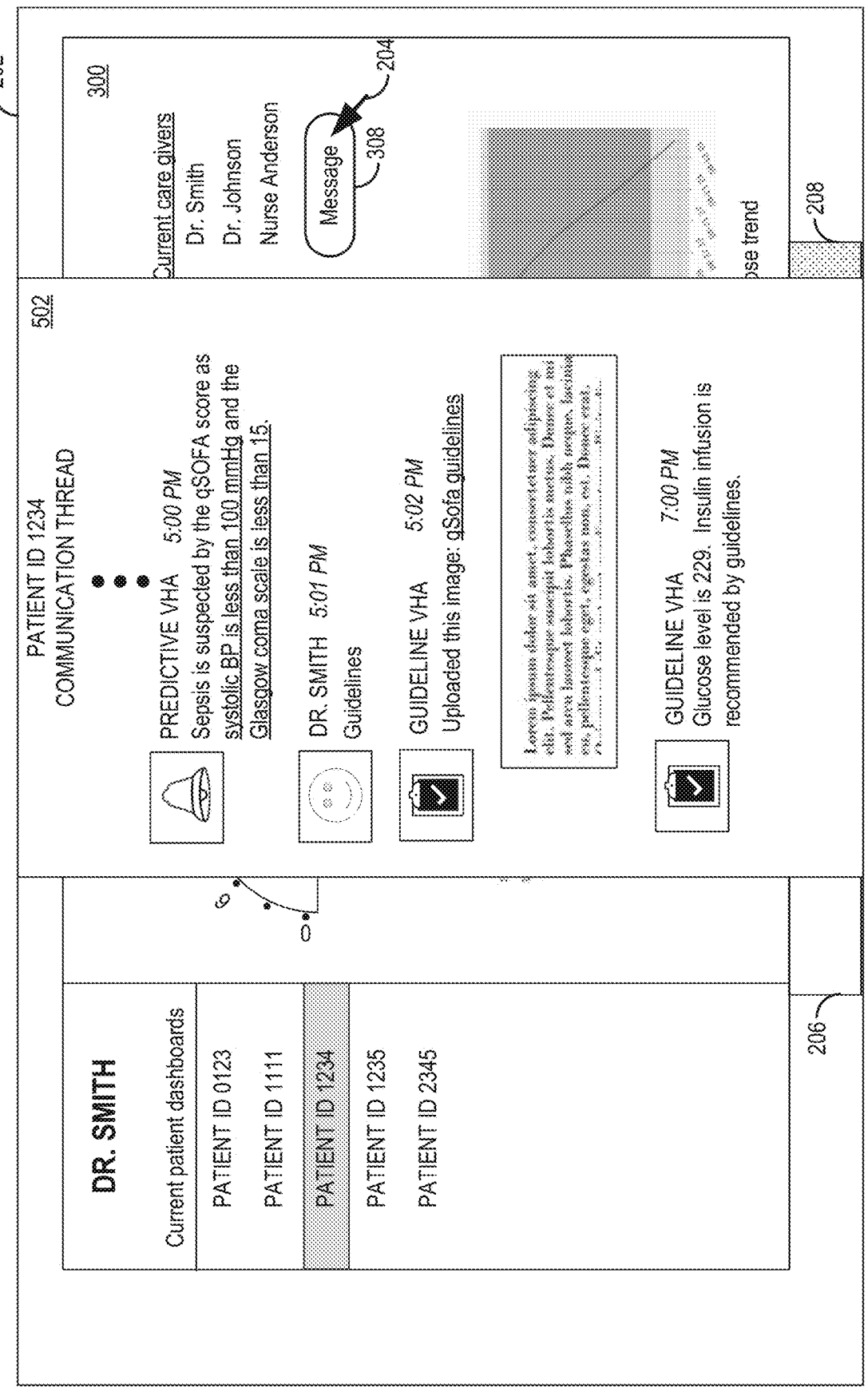
FIG. 5 shows an example display device displaying the dashboard of FIG. 3 including display of a full version of the communication thread of FIG. 2.
Figure 6:
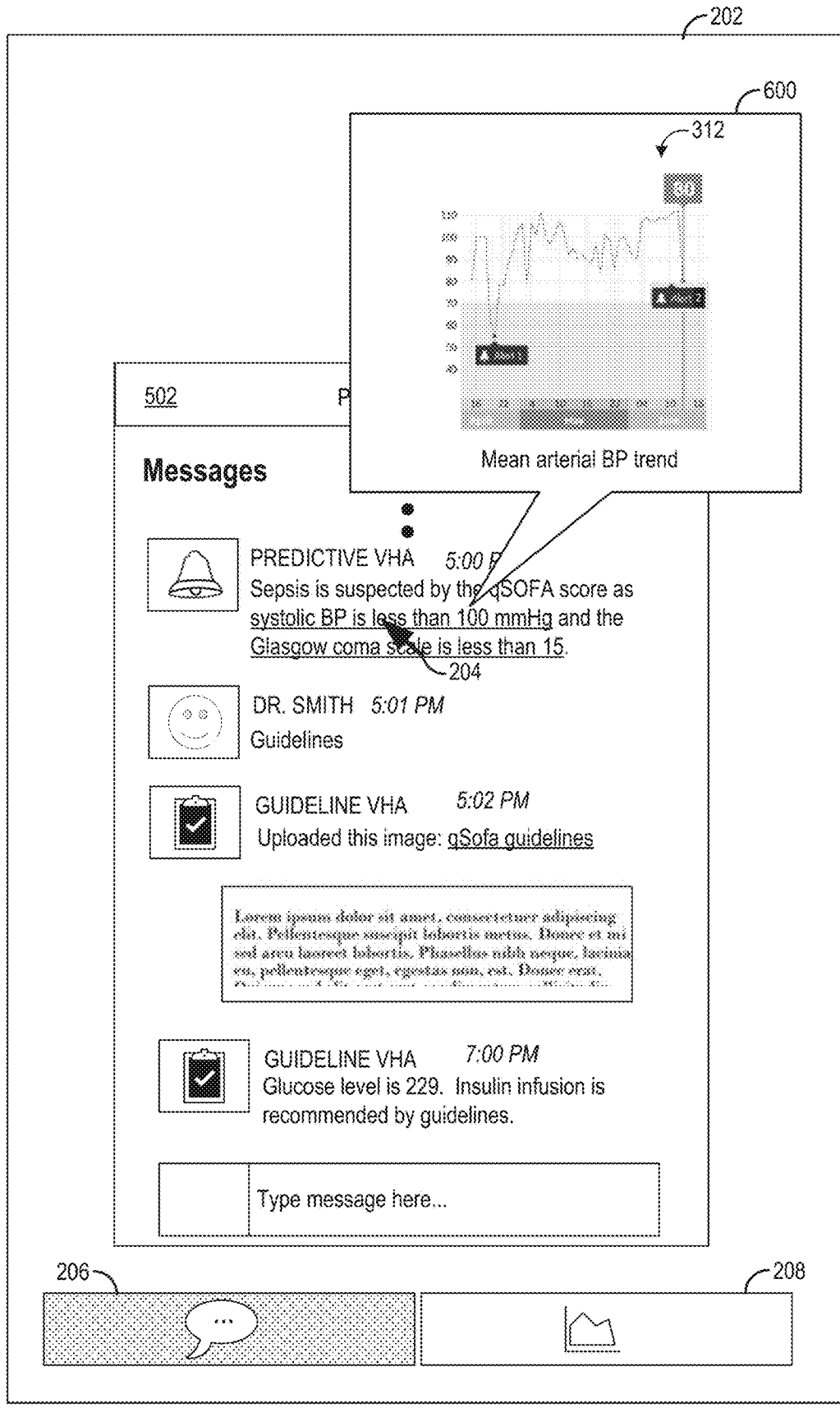
FIG. 6 shows an example display device displaying the communication thread of FIG. 2 including display of a preview of the dashboard of FIG. 3.
Figure 10:
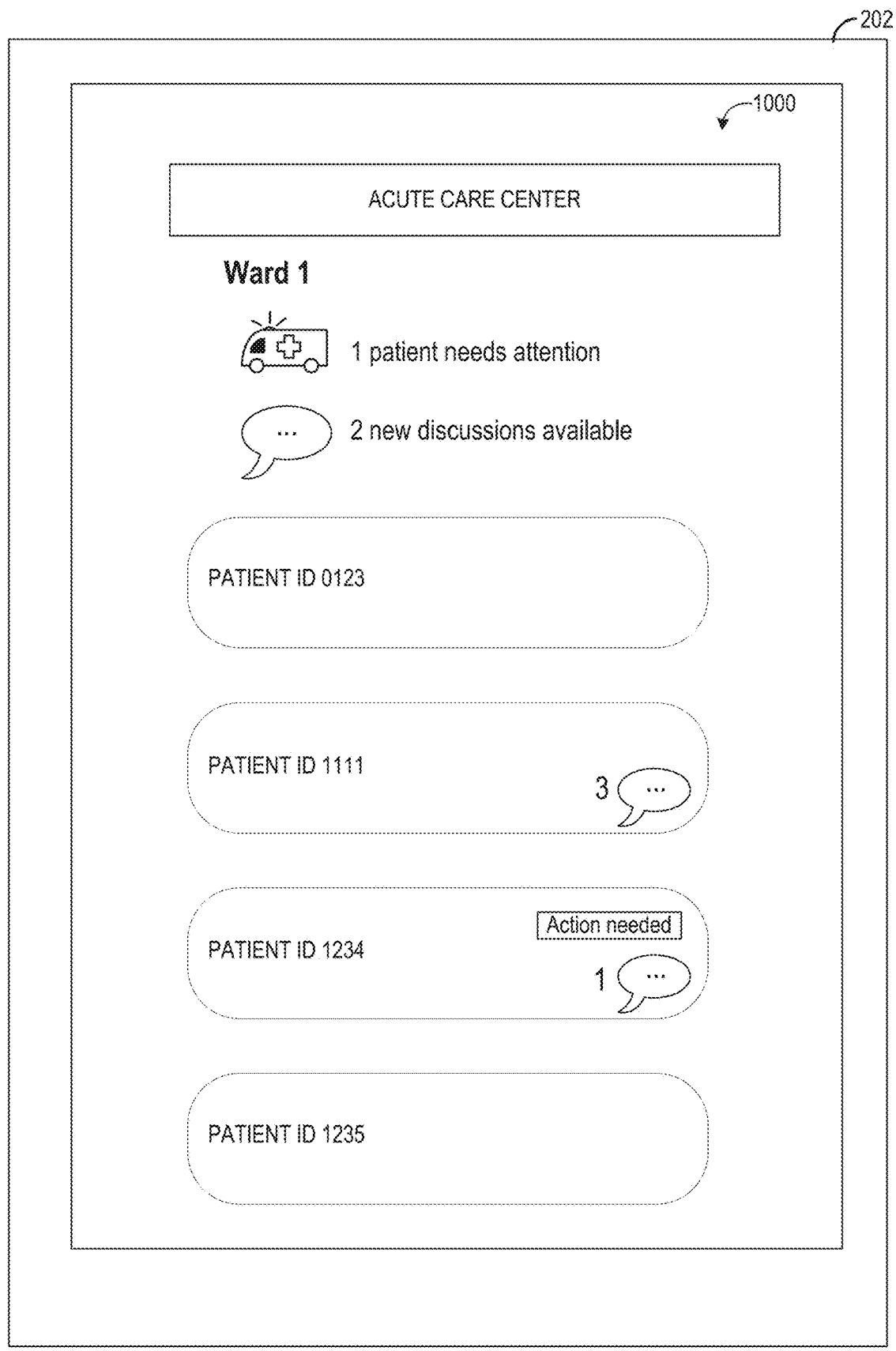
FIG. 10 shows an example display device displaying a collaborative interface.

An example collaborative healthcare system is shown in FIG. 1. The collaborative healthcare system may be included in or associated with a medical facility and may include a communication channel comprising a communication thread and a dashboard for each admitted patient of the medical facility. The collaborative healthcare system may further include one or more virtual healthcare assistants. Communication may occur on a communication channel in the form of a communication thread (e.g., of text and/or rich media messages) between care providers of the patient and the one or more virtual healthcare assistants, as shown in FIG. 2. Patient-specific medical information may be displayed to the care providers and/or other users via a dashboard. As shown in FIG. 3, the dashboard may be launched in response to a first selection of a link on the communication thread. The dashboard may be configured to display alerts output by the one or more virtual healthcare assistants, and the alerts may be selectable to launch a portion of the communication thread occurring on the communication channel, as shown in FIG. 4. The dashboard may be further configured to display a control button selectable to launch a full version of the communication thread, as shown in FIG. 5. As shown in FIG. 6, a preview of the dashboard may be launched in response to a second selection of a link on the communication thread. Further, a collaborative system interface, as shown in FIG. 10, may be displayed on a suitable display device in order to allow a user to select a communication channel or dashboard to view.

Figure 7:
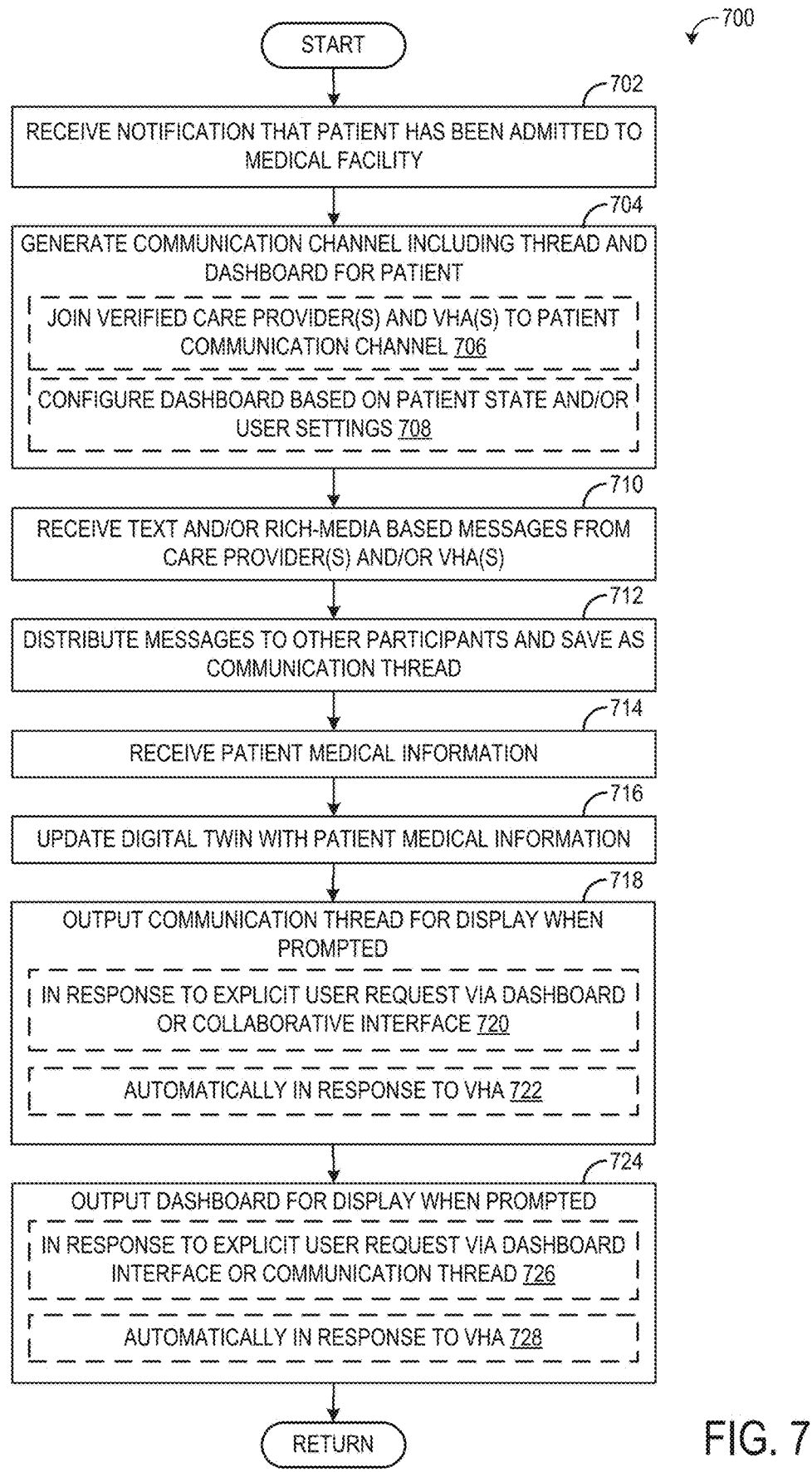
FIG. 7 is a flow chart illustrating an example method for facilitating communication within a collaborative healthcare system.
Figure 8:
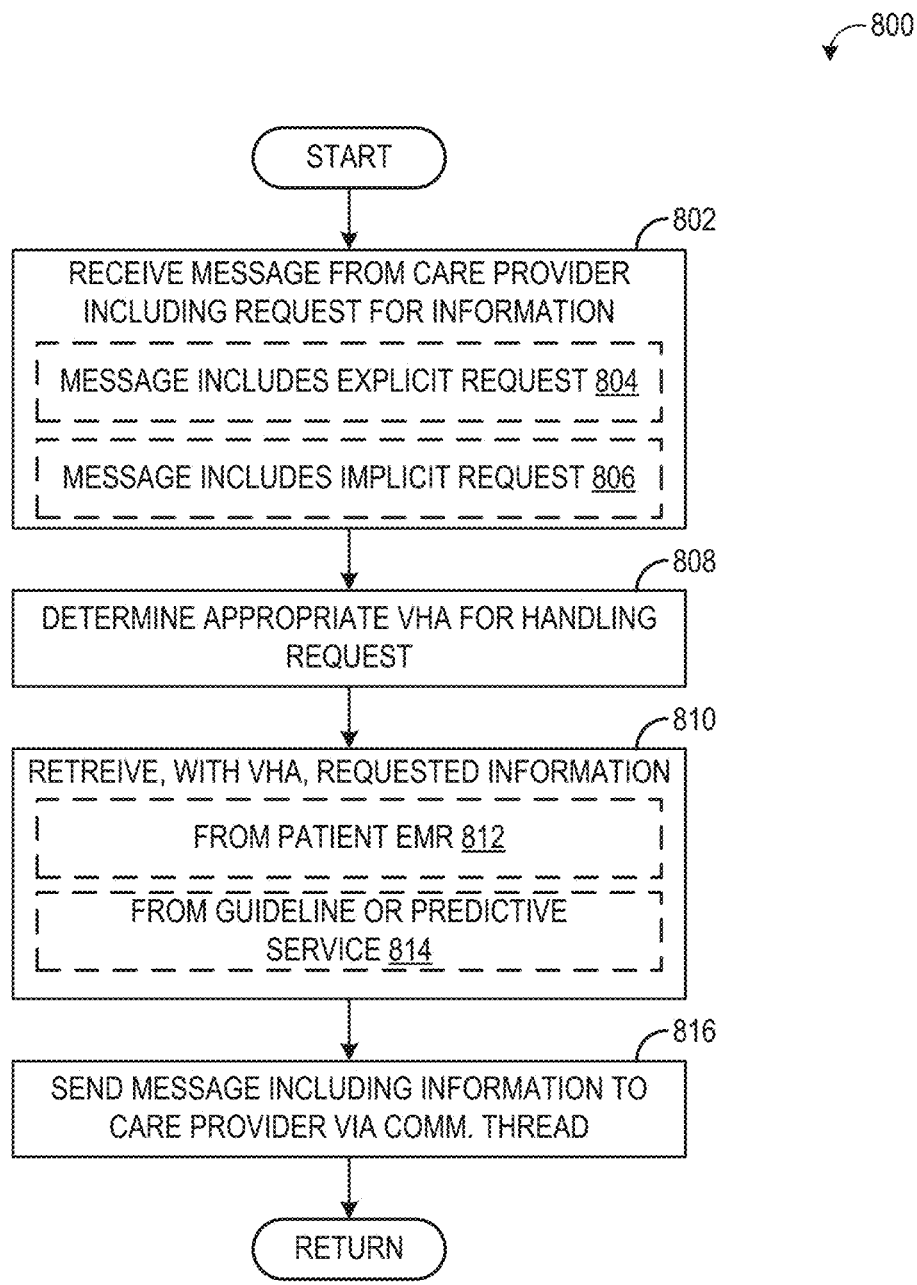
FIGS. 8 and 9 are flow charts illustrating example methods for one or more virtual healthcare assistants of the collaborative healthcare system.

The communication thread-dashboard pairs may be generated and accessed according to the method illustrated in FIG. 7. The virtual healthcare assistants may provide assistant to the care providers of the patient by retrieving medical information of the patient from an electronic medical record, providing treatment or care guidelines, and/or providing predications of future patient states, as shown by the method of FIG. 8. The virtual healthcare assistants may further be configured to monitor the condition/state of the patient and notify the care providers if the virtual healthcare assistants determine the state or condition of the patient has changed, as shown in the method illustrated in FIG. 9.

FIG. 1 schematically shows an example collaborative healthcare system 100 that may be implemented in medical facility such as a hospital. Collaborative healthcare system 100 may include a collaborative space server system 102. Server system 102 may include resources (e.g., memory 130, processor(s) 132) that may be allocated to store and execute a communication thread, a dashboard, and a digital twin for each of a plurality of patients. For example, as shown in FIG. 1, a communication thread 104, dashboard 106, and digital twin 108 are stored on server system 102 for a first patient (patient 1); a plurality of additional communication threads, dashboards, and digital twins may be stored on server system 102, each corresponding to a respective patient (patient 2 up to patient N).

As explained above, the communication thread 104 may facilitate communication among multiple care providers that are each providing care to the patient (e.g., patient 1) as well as one or more virtual healthcare assistants (explained in more detail below). Messages sent on the communication thread 104 may be saved and may be accessible via the dashboard 106 (and the dashboard may be accessible via the communication thread). Further, the patient medical information, including medical history, current state, vital signs, and other information, may be entered to the digital twin 108, which may be used to gain situational awareness, clinical context, and medical history of the patient to facilitate predicted patient states, procurement of relevant treatment guidelines, patient state diagnoses, etc.

Communication occurring on communication thread 104 may be displayed on one or more suitable display devices associated with a respective care provider device and/or medical facility administration device. Likewise, dashboard 106 may be displayed on the one or more display devices. As shown in FIG. 1, a plurality of care provider devices, from a first care provider device 134, a second care provider device 136, and on up to an nth care provider device 138, may be communicatively coupled to server system 102. Each care provider device may include a processor, memory, communication module, user input device, display (e.g., screen or monitor), and/or other subsystems and may be in the form of a desktop computing device, a laptop computing device, a tablet, a smart phone, or other device. Each care provider device may be adapted to send and receive encrypted data, display medical information, including medical images in a suitable format such as digital imaging and communications in medicine (DICOM) or other standards, and ensure only authenticated users have access to patient medical information. The care provider devices may be located locally at the medical facility (such as in a nurse's station or in the room of a patient) and/or remotely from the medical facility (such as a care provider's mobile device).

When viewing communication thread 104 and/or dashboard 106 via a display of a care provider device, a care provider may enter input (e.g., via the user input device, which may include a keyboard, mouse, microphone, touch screen, stylus, or other device) that may be processed by the care provider device and sent to the server system 102. In examples where the user input is a message to be sent to other care providers and/or one or more virtual healthcare assistants, the message may be sent to the server system 102, where the message may be saved as part of the communication thread 104 and then the server system 102 may send the message to other verified participants on the communication channel (e.g., the other care providers and/or one or more virtual healthcare assistants that are joined to the communication channel). In examples where the user input is a selection of a link or user interface control button of the dashboard, the user input may trigger display of the communication thread, trigger progression to a desired state of the dashboard (e.g., trigger display of desired patient medical information), trigger updates to the configuration of the dashboard, or other actions.

The collaborative space server system 102 may be communicatively coupled to hospital operational systems 118. The hospital operational systems 118 may store and/or control a variety of hospital-, care provider-, and patient-related information, including but not limited to patient admission information (including date of admission and location of the patient within the medical facility), patient care protocols and workflows, and care provider information including which care providers are monitoring/treating which patients. Further, the hospital operational systems 118 may be communicatively coupled to a plurality of monitoring devices 120, an electronic medical records (EMR) database 122 (described in more detail below), and one or more of the care provider devices. The monitoring devices 120 may include traditional medical devices monitoring respective patients, such as pulse oximeters, heart rate monitors, blood glucose monitors, ECGs, and medical imaging modalities (e.g., ultrasound, CAT, MM), as well as microphones, cameras, and other devices. The monitoring devices 120 may send output directly to the server system 102 and/or may send output to the hospital operational systems 118, EMR database 122, and/or one or more care provider devices. For example, a plurality of monitoring devices monitoring patient 1 may be configured to send output to a care provider device (care provider device 134), and the care provider device may be configured to send some or all of the data output by the monitoring devices to the server system 102.

The hospital operational systems 118 may direct creation of and control access to each communication thread and dashboard. For example, when a patient is admitted, the hospital operational systems 118 may associate the patient with an identifier (e.g., an identification code) and notify the collaborative space server system 102 to generate a communication channel for that patient. When a care provider is assigned to assist in management/treatment of the patient, the hospital operational systems 118 may notify the collaborative space server system 102 to join that care provider to the patient's communication channel (the care provider may also be associated with an identifier which may be used to identify the care provider and appropriately distribute messages sent and received on the channel). In this way, the hospital operational systems 118 may control who has access to patient information and may rely on biometric or other means of authenticating users, as well as controlling levels of accessibility depending on location of a care provider device (e.g., devices located at the medical facility may have access to more patient information than devices located remotely from the medical facility). Additional information about the hospital operational systems 118 is presented below.

Collaborative space server system 102 may further store instructions for (e.g., in memory 130) and be configured to execute (e.g., via processor(s) 132) a plurality of virtual healthcare assistants (VHAs). As shown, collaborative space device 102 includes an electronic medical record (EMR) VHA 110, a guideline VHA 112, a predictive VHA 114, a listening VHA 116, and a monitoring VHA. The VHAs may be realized as several VHAs each for a different purpose, as described herein, various groups of VHAs (e.g., the guideline VHA 112 and predictive VHA may be combined into one VHA that is configure to both diagnosis or predict patient state and output relevant guidelines), or as one overall VHA, which represents all the different attributes that will be hereby elaborated. All activations of VHAs by human care providers may be performed by using natural language including medical language, either by text or by voice.

EMR VHA 110 is configured to retrieve patient information from an electronic medical record database, such as EMR database 122, and present the retrieved data via the communication thread and/or dashboard. For example, a care provider may send a request to the EMR VHA 110, through the communication channel, for a particular piece of patient medical history saved in an EMR of the patient. The EMR VHA 110 may receive the request and determine, from the natural language of the text, that the piece of patient medical history has been requested. The EMR VHA 110 may obtain the piece of medical history from EMR database 122. The EMR VHA 110 may then send the piece of medical history to the care provider in the form of a message on the communication thread 104. In some examples where the requested piece of medical history is also saved in the digital twin 108, EMR VHA 110 may be configured to retrieve the medical history from the digital twin 108.

EMR database 122 may be an external database accessible by EMR VHA 110 via a secured hospital interface, or EMR database 122 may be a local database (e.g., housed on a device of the hospital). EMR database 122 may be a database stored in a mass storage device configured to communicate with secure channels (e.g., HTTPS and TLS), and store data in encrypted form. Further, the EMR mass storage device is configured to control access to patient electronic medical records such that only authorized healthcare providers may edit and access the electronic medical records. An EMR for a patient may include patient demographic information, family medical history, past medical history, preexisting medical conditions, current medications, allergies, surgical history, past medical screenings and procedures, past hospitalizations and visits, etc.

Thus, the EMR VHA 110 serves as a connection to the EMR database. The EMR VHA may interpret questions by the human care providers regarding the patient and allows querying the EMR database for relevant information regarding the patient (e.g. "what was the average systolic blood pressure in the last four hours?" or "show me the trend of the O2 saturation"). Queries can implicitly relate to the patient's status or medical history. The EMR VHA 110 also allows EMR-generated alerts to be formatted and sent into the patient communication thread (in a configurable manner either by a "setting" option or by voice command, such as telling it, e.g., "don't show me this again"). The EMR VHA 110 may also serve as a drug safety alerting system (including allergies, drug-to-drug relations, etc.) and may be thus connected to a relevant medical knowledgebase.

Guideline VHA 112 is configured to retrieve relevant care guidelines from an external guideline service 124. Guideline VHA 112 may be prompted, via communication occurring on communication channel, to retrieve care guidelines. For example, a care provider may explicitly request care guidelines for a given condition, such as sepsis, on the communication thread and guideline VHA 112 may query external guideline service 124 in response to the explicit request. In other examples, guideline VHA 112 may determine implicitly that care guidelines for a given patient condition are being requested and/or may be helpful. For example, guideline VHA 112 may parse communication on the communication thread 104 (e.g., between one or more care providers and/or a suitable VHA) to determine that guidelines are being requested (e.g., rather than receiving an explicit request for the guidelines, guideline VHA 112 may determine that two care providers are discussing guidelines and may retrieve the guidelines without being requested to do so). In a further example, guideline VHA 112 may determine, from patient vital signs (e.g., output by the one or more monitoring devices 120), digital twin 108, and/or other sources that a patient may be undergoing a given condition (e.g., high heart rate) and may automatically obtain guidelines for treating the condition.

External guideline service 124 may be a remote service accessed via a network, or external guideline service 124 may be a local service executed on a computing device of the hospital. The care guidelines obtained from external guideline service 124 may be preconfigured by protocols and guidelines that are specific to the medical facility that the collaborative space server system 102 services. Further, external guideline service 124 may include differential diagnoses trees that guideline VHA 112 may access to determine potential diagnoses based on a patient condition or state.

For example, with regards to the patient's state and medical history as search terms, e.g., if a diabetic patient has a high sequential organ failure assessment (SOFA) score and high glucose levels, specific guidelines will be queried without additional query terms, or alternatively the external guideline service may be queried by specifying specific guidelines. In other words, the guideline VHA may enter specific search terms to the guideline service based on patient state and symptoms (e.g., diabetes, SOFA score of five, glucose level of 190 mg/dL) to obtain one or more potential diagnoses and/or guidelines, or the guideline VHA may specifically ask for guidelines for a given condition (e.g., sepsis). The guideline VHA may also serve as a source for generating reminders for treatments that are part of a care protocol or to keep track of what decision-driving tests have been completed and what are still needed to complete the protocol. A change in patient status may be a trigger for automatic notification of relevant guidelines. The guideline VHA may also be used to plan a trajectory for the patient, of both disease progressing and a care path. In doing so, the guideline VHA may assist care providers to stay the course and give early warning if the patient deviates from the planned trajectory.

Predictive VHA 114 is configured to retrieve predictions of future patient states from an external prediction service 126. Predictive VHA 114 may detect and issue alerts on relevant changes in the patient's state (e.g., small but worrying changes in vital signs, changes in qSOFA score). Predictive VHA 114 may also predict future events (e.g., a prediction of sepsis being developed in the coming four hours) by connecting to external prediction service 126. Predictive VHA 114 may query external prediction service 126 with search terms indicating current and/or past patient state (e.g., blood pressure trend, glucose level trend, etc.). If prediction service 126 outputs a possible future condition, the predictive VHA 114 may send an alert into the communication thread, as text, and may provide supplemental information regarding the alert. The predictive VHA 114 may also track the response of human care providers as reflected in the communication channel or in the EMR orders registry. The predictive VHA 114 may obtain patient data from the EMR and different online monitoring devices 120 (ECG, cameras, etc.) as represented in the digital twin.

Listening VHA 116 is configured to monitor communication on the communication channel 104 as well as actual human voice communication to obtain/infer various information related to the patient. In doing so, listening VHA 116 serves as a monitor, by listening to the events in the patient's surroundings including medical staff conversations and patient's input (from moaning to speech). The monitored conversations/inputs may be used to record the patient's status (for EMR/digital twin) or to infer clinician reasoning (e.g., the listening VHA may catch an order to prescribe a certain antibiotic by a doctor, and understand an infection is suspected). The listening VHA 116 may receive output from one or more microphones positioned in proximity to the patient, for example, in order to monitor the conversations and inputs.

Monitoring VHA 117 is configured to receive output from the monitoring devices 120 and may track a patient condition or state based on the received output. In some examples, monitoring VHA 117 may present the received data via the communication thread and/or dashboard. For example, a care provider may send a request to the monitoring VHA 117, through the communication channel, for a particular piece of patient monitoring data, such as current heart rate. The monitoring VHA 117 may receive the request and determine, from the natural language of the request, that the patient medical data has been requested. The monitoring VHA 117 may obtain the patient medical data from the relevant monitoring device of the monitoring devices 120. The monitoring VHA 117 may then send the medical data to the care provider in the form of a message on the communication thread 104. In some examples, monitoring VHA 117 may be configured to save the medical data at the digital twin 108. Further, medical data received by monitoring VHA 117 may be displayed via the dashboard. In some examples, monitoring VHA 117 may obtain patient medical data only in response to a request from a care provider. In other examples, additionally or alternatively, monitoring VHA 117 may obtain medical data from the monitoring devices 120 independently of care giver request, and may output requested medical data when a care giver requests the data and/or when the received medical data is detected (by the VHA) as being abnormal, having changed, or otherwise indicative of an urgent patient state. In some examples, monitoring VHA 117 may be configured to provide received medical data to predictive VHA 114 and/or guideline VHA 112 in order to predict a future patient state based on current patient medical data and/or retrieve relevant care guidelines based on current patient medical data.

The VHAs may be configured to receive messages from human care providers and utilize natural language processing to determine what information is being conveyed in the messages. For example, the VHAs may utilize natural language processing to determine if a message received on the communication channel includes a request for patient medical information, and if so, determine what medical information is being requested. The VHAs may also be configured to process medical information of the patient (e.g., vital signs, medical history, current symptoms) received from the patient EMR, the monitoring devices, the care providers, and/or other sources and determine which parameters of the medical information may be used (e.g., entered into the guideline or prediction service) to determine a patient state (such as determine the likelihood the patient is experiencing a certain condition, such as sepsis). The VHAs may be trained using machine learning (e.g., deep learning), such as neural networking or other training mechanisms that are specific to medical terminology. Further, the VHAs may be configured to learn the above-described parameters in a patient and/or care provider specific manner. For example, a predictive VHA may be trained to determine that low blood pressure may be a symptom of relevance that should be entered into a prediction service or diagnosis tree, but then may be trained for a specific patient that low blood pressure for that patient is benign and may have less relevance.

The VHAs may be trained in a suitable manner. In a first example, the VHAs may be rule-based assistants that are configured with a set of answers for predetermined, likely questions. When a VHA receives a question, the VHA may be configured to output an answer from the set of answers.

In a second example, the VHAs may include directed acyclic graphs (DAG) of states, each of which include rules for how to react and how to proceed to various questions. However, such VHAs may only be configured to respond when there is a clear indication of the user intent (e.g., the user presses on a button "obtain heart rate") and entities (answer to "please provide the patient's date of birth" with a date).

Thus, the VHAs described herein may include artificial intelligence and be adapted to handle natural language which is a way to take human input and map it to intent and entities. The VHAs may be adapted to hold a state and map the state with (intent, entities) to an actionable API. The mapping may be performed by teaching a machine learning model by providing the VHAs with examples of such mappings. If a VHA is autonomous, the VHA may include a prediction or other mechanism that may trigger the VHA to initiate communication. The VHAs may also be configured to vary their reactions to make the VHAs more human like (this may also be performed by providing examples to a machine learning training algorithm).

Further, the training mechanism utilized may be specific for different VHAs. For example, the listening VHA (and the natural language processing engines of the other VHAs) may be trained by using deep networks for natural language with medical language. This may be combined with taxonomies from the medical domain. The EMR VHA and the guideline VHA may receive the output (intent and entities) from the listening VHA and/or the respective natural language processing engine and map the output to queries. The VHAs may be trained by having examples of the best results of existing queries. The predictive VHA may be trained on its own clinical task. For example, if the predictive VHA is to predict if a patient will survive early release from an intensive care unit, then the predictive VHA may be trained on data of patients that were in the ICU and were released at different stages.

Additional VHAs may be included on the server system, such as VHAs specific to a patient state. Such an example may include a sepsis VHA that may only be joined to a patient communication channel when that patient is undergoing or at risk of developing sepsis. The sepsis VHA may be trained to specifically predict sepsis and obtain treatment guidelines for sepsis. Other VHAs may include a patient comfort VHA (e.g., a VHA configured to detect or predict patient pain, discomfort, hunger, or other symptoms not necessarily indicative of a particular medical condition but which care providers may want to be notified of to improve patient comfort), a communication VHA (e.g., that parses communication from care givers and facilitates sharing of information among the VHAs), and/or other VHAs. Further, various configurations of VHAs not disclosed above are within the scope of this disclosure, such as related VHAs being grouped into a single VHA (e.g., the monitoring and EMR VHAs being combined as one medical data VHR).

A global view of multiple or all patient communication thread-dashboard pairs may be provided via to one or more of the care provider devices and the hospital operational systems 118. For example, the choice of the specific thread/dashboard pair to access may be controlled by an access application executing on collaborative space server system 102 that allows to a user to view all the relevant patients (for example, communication thread-dashboard pairs for all the patients being treated/monitored in a nurses station may be accessed on a workstation at the nurses station, or communication thread-dashboard pairs for all the patients being treated/monitored by a given care provider may accessed by that care provider on his or her mobile device). In some examples, alerts and important events within all the relevant communication channels will be signified in the global view. The choice to go into a specific communication channel may be made by a user picking the patient in the global view (or by an explicit voice command), but may be also be automated using automatic mechanisms which may detect the position of the care provider in respect to a patient (such as via BLUETOOTH® when entering a patient's proximity or based the context of a detected discussion).

The access application may allow export of only specific widgets (such as the blood pressure graph of a patient) of a communication thread and/or dashboard, or may allow more compound parts (such as a patient dashboard or a portion of the thread) to selected external applications and/or devices. For example, as explained above, devices located off-site of the medical facility may only be allowed access to some of the patient medical data, and the access application may control which patient medical data is viewable outside of the medical facility.

A management application executed on hospital operational systems 118 and/or collaborative space server system 102 may allow an administrator to update the care team that has access to a patient's communications channel, as described above. The management application may include an interface for configuring hospital specific protocols and care guidelines. The management application may also aggregate information from the communication channels to be used to predict needs for hospital operations, presenting forecasts for capital, disposable, and human assets based on aggregate acuity or disease statistics. Moreover, analytics of the information on the communication channel may be employed to improve the system and its predictors.

Collaborative space server system 102 includes a communication module 128, memory 130, and processor(s) 132 to store and execute the communication channel-dashboard pairs, digital twins, and VHAs, as well as send and receive communications, graphical user interfaces, medical data, and other information.

Communication module 128 facilitates transmission of electronic data within and/or among one or more systems. Communication via communication module 128 can be implemented using one or more protocols. In some examples, communication via communication module 128 occurs according to one or more standards (e.g., Digital Imaging and Communications in Medicine (DICOM), Health Level Seven (HL7), ANSI X12N, etc.). Communication module 128 can be a wired interface (e.g., a data bus, a Universal Serial Bus (USB) connection, etc.) and/or a wireless interface (e.g., radio frequency, infrared, near field communication (NFC), etc.). For example, communication module 128 may communicate via wired local area network (LAN), wireless LAN, wide area network (WAN), etc. using any past, present, or future communication protocol (e.g., BLUETOOTH™, USB 2.0, USB 3.0, etc.).

Memory 130 one or more data storage structures, such as optical memory devices, magnetic memory devices, or solid-state memory devices, for storing programs and routines executed by processor(s) 132 to carry out various functionalities disclosed herein. Memory 130 may include any desired type of volatile and/or non-volatile memory such as, for example, static random access memory (SRAM), dynamic random access memory (DRAM), flash memory, read-only memory (ROM), etc. Processor(s) 132 may be any suitable processor, processing unit, or microprocessor, for example. Processor(s) 132 may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. In certain examples, users (e.g., a patient and/or care provider) can access functionality provided by collaborative space server system 102 via a software-as-a-service (SaaS) implementation over a cloud or other computer network, for example. In certain examples, all or part of server system 102 can also be provided via platform as a service (PaaS), infrastructure as a service (IaaS), etc. For example, server system 102 can be implemented as a cloud-delivered Mobile Computing Integration Platform as a Service. A set of consumer-facing Web-based, mobile, and/or other applications enable users to interact with the PaaS, for example. Further, while server system 102 is shown in FIG. 1 as constituting a single entity, it is to be understood that server system 102 may be distributed across multiple devices, such as across multiple servers and/or the cloud.

While not specifically shown in FIG. 1, additional devices described herein (care provider device 134, care provider device 136, and care provider device 138, hospital operational systems 118, monitoring devices 120, EMR database 122, external guideline service 124, external prediction service 126) may likewise include user input devices, memory, processors, and communication modules/interfaces similar to communication module 128, memory 130, and processor(s) 132 described above, and thus the description of communication module 128, memory 130, and processor(s) 132 likewise applies to the other devices described herein. As an example, the care provider devices (e.g., care provider device 134) may store user interface templates in memory that include placeholders for relevant information stored on server system 102. For example, care provider device 134 may store a user interface template for a patient dashboard that a user of care provider device 134 may configure with placeholders for desired patient information. When the dashboard is displayed on the care provider device, the relevant patient information may be retrieved from server system 102 and inserted in the placeholders. The patient information may include current patient vital signs, VHA alerts, desired patient state trends, or other information, as explained in more detail below. The user input devices may include keyboards, mice, touch screens, microphones, or other suitable devices.

FIG. 2 shows an example communication thread 200 of a patient-specific communication channel, and as such may be a non-limiting example of communication thread 104. Communication thread 200 may be displayed on a display device 202. Display device 202 may include a screen on which the communication thread is displayed and may be coupled to and/or included as a part of a computing device, such as care provider device 134. Communication thread 200 may be displayed in response to a user request to display the communication thread. For example, the user (e.g., a care provider) may access a collaborative system interface that includes a global view of all communication threads and dashboards the user is authenticated to participate in (which may include all patients at the medical facility the care provider is attending to) and may select a desired communication thread to view. An example collaborative system interface 1000 is shown in FIG. 10. Collaborative system interface 1000 may be displayed on display device 202 or other suitable device and may include all patients admitted to a specific unit or ward of a medical facility. As shown, collaborative system interface 1000 includes identifying information specifying the medical facility ("acute care center") and relevant unit ("ward 1") of the medical facility, and further includes links to patient-specific communication threads and dashboards for the patients in that unit of that medical facility. However, in other examples, the patients shown via collaborative system interface 1000 may be specific to a certain care provider.

Collaborative system interface 1000 may include a notification section whereby the user viewing collaborative system interface 1000 may be notified of urgent patient conditions, active communication channel discussions, and other information. For example, collaborative system interface 1000 includes a notification section that shows that one patient requires attention (e.g., due to deteriorating vital signs) while two new discussions are available.

Collaborative system interface 1000 further includes links to patient communication thread-dashboard pairs. For example, FIG. 10 shows links to communication thread-dashboard pairs for patient ID 0123, patient ID 1111, patient ID 1234, and patient ID 1235. As explained above, each patient may be assigned an identifier that may be used to identify the patient on the communication thread and dashboard. In other examples, other mechanisms for identifying the patient may be used, such as location (e.g., bed 2 in room 4) or actual patient name. Additional patient links may be viewed by scrolling the interface. Each patient link may include notifications where relevant. For example, the link for patient ID 1111 includes a notification that three new messages are available to be viewed on the communication channel for that patient. The link for patient ID 1234 includes a notification that action is needed (e.g., due to high blood pressure or other significant vital sign being detected, which will be explained in more detail below) as well as a notification that one new message is available on the communication channel for that patient.

Selection of a patient link may launch the communication thread or dashboard for that patient. For example, selection of the link for patient ID 1234 may launch the communication thread 200 for patient ID 1234, shown in FIG. 2 and explained in more detail below.

Returning to FIG. 2, communication thread 200 may include an identification header that identifies the patient being discussed/monitored via the communication thread. In the illustrated example, communication thread 200 is specific to patient ID 1234. In the illustrated portion of communication thread 200, communication is occurring between a care provider (Dr. Smith) and three virtual healthcare assistants, an EMR VHA, a predictive VHA, and a guideline VHA. Communication thread 200 is being viewed by Dr. Smith, although any authenticated/approved user may view communication thread 200. As shown by the first message from the top, Dr. Smith is requesting medical information relating to the patient from one of the VHAs by asking, in natural language, for a heart rate graph ("Could I get the HR graph please"). In response, the EMR VHA sends an image of the patient's heart rate, which may be obtained from the patient's EMR. The image of the heart rate is viewable in the communication thread and may also be selected via suitable user input to view in a different form, such as via the patient dashboard.

At a later time (e.g., 4:00 PM), the predictive VHA outputs an alert/notification in the communication thread indicating a change in patient status, herein a deterioration in vitals. The alert is accompanied by a suggested course of action that a care provider may take, including checking respiratory rate and mental state. The predictive VHA issues another alert at 5:00 PM indicating that sepsis is suspected based on a quick SOFA score (qSOFA), owing to low systolic blood pressure and a low Glasgow coma scale. The alerts issued by the predictive VHA may include links to the patient dashboard, for example, allowing a user to select a link to launch the dashboard and view the medical data relating to the alerts. For example, the alert "systolic BP is less than 100 mmHg" is shown in underline, indicating a link to additional information is available. A user may select the link via a suitable input, such as via a mouse click, touch input, or voice command. As shown, the user may select the link with a cursor 204. As will be explained in more detail below, selecting the link with a first selection (e.g., a double click) may launch the patient dashboard (as shown in FIG. 3). Selecting the link with a second selection (e.g., a single click or a hover) may launch a preview where only the patient's blood pressure graph is shown (as explained in more detail below with respect to FIG. 6).

In response to the alert regarding the potential sepsis, Dr. Smith asks for guidelines at 5:01 PM. Because the predictive VHA had immediately previously issued the alert regarding the possible sepsis due to the qSOFA score, the guideline VHA may assume that the guidelines being requested by Dr. Smith include guidelines for sepsis based on a qSOFA score. In response, the guideline VHA retrieves guidelines from an external guideline service relating to qSOFA scores and outputs the guidelines into the communication thread. As shown, only a portion of the guidelines are displayed in the communication thread. By selecting the link (the underlined "qSofa guidelines"), the user may be taken to a different interface where the full guidelines are displayed, or the full guidelines may be displayed over the top of the still-displayed communication thread.

While not shown in FIG. 2, communication thread 200 may include a search box/functionality where a user may search for past messages on the communication thread. For example, a user may enter a command (by voice or text) requesting that all messages related to the patient's heart rate be displayed. Also displayed on display device 202 is a communication thread button 206 and a dashboard button 208. In FIG. 2, the user is viewing the communication thread 200 occurring on the communication channel. Hence, the communication thread button 206 is highlighted. To switch to the dashboard for patient ID 1234, the user may select the dashboard button 208.

FIG. 3 shows an example dashboard 300 that may be displayed on display device 202 or any other suitable device. Dashboard 300 may be displayed in response to a user input to the communication thread 200, for example by selecting a link within medical information displayed in communication thread, as explained above, or in response to selection of the dashboard button 208. However, dashboard 300 may be displayed in response to other inputs, such as in response to a user input selecting the dashboard from the collaborative system interface of FIG. 10 that includes a global view of multiple communication threads and dashboards. Additionally, FIG. 3 shows a side bar 302 displayed along with dashboard 300 showing patient dashboards for the patients Dr. Smith is currently attending. User input to the side bar may launch a different dashboard, for example Dr. Smith may select to view each of the currently available dashboards to quickly assess the status of each patient.

Dashboard 300 may be configured to display patient medical information based on the current patient state and user-configured settings. For example, a dashboard for a patient that is being treated at the medical facility for pneumonia may be configured to display different medical information than a dashboard for a patient that is being treated at the medical facility for a stroke. In some examples, when a patient is admitted at the medical facility, a dashboard may be generated automatically for the patient based on the reason of admittance (e.g., pneumonia), thereby including the most relevant patient medical information for the patient's condition, such as blood oxygen level and respiration rate. A user may also configure which medical data to view via the dashboard, for example a doctor attending to the patient may choose to view heart rate rather than respiration rate.

The medical information that is displayed on the dashboard may be obtained from one or more monitoring devices currently monitoring the patient, such that the medical information is displayed on the dashboard in a real-time (or near real-time) manner. Additionally or alternatively, the medical information that is displayed on the dashboard may be obtained from the patient's EMR, the digital twin associated with the patient, and/or the communication thread. As explained above, one or more VHAs may obtain patient medical information from the patient's EMR, the monitoring devices, guideline services, or other sources and include the obtained medical information as a message in a communication thread on the communication channel. To view the medical information in greater detail, the user may select the medical information from the communication thread, where the medical information may then be displayed in the dashboard.

Additional information may also be displayed via the dashboard, such as patient information (location, demographics, medical history), care provider information (such as which doctors, nurses, and/or other care providers are attending to the patient), and a timeline of selected or relevant messages from the communication thread. For example, the most recent alerts may be displayed as a timeline on the dashboard.

Referring to dashboard 300 as an example, patient information 304 is displayed at the top of the dashboard, including patient identification and location. Care provider information 306 is also displayed in dashboard 300, including current care providers for the patient. Additionally, a user interface control button 308 is shown that, when selected, may allow the care provider viewing dashboard 300 to view and interact with the communication thread.

Dashboard 300 further includes real-time medical information indicators 310. As shown, the indicators 310 include a SOFA score and blood glucose level, depicted as gauge charts with respective needles that move to indicate current SOFA score and blood glucose relative to a range of possible SOFA scores and blood glucose levels. While not shown in FIG. 3, the gauge charts may include color coding for quick determination of normal, intermediate, and high scores/levels, for example. The gauge charts shown are exemplary in nature and patient medical information may be shown in other forms.

Dashboard further includes medical history trends, including a first graph 312 depicting mean arterial blood pressure trend (e.g., blood pressure as a function of time) and a second graph 314 depicting blood glucose trend (e.g., blood pressure as a function of time). The medical history trends shown in FIG. 3 may be displayed on the dashboard in response to a request from a user (e.g., in response to a care provider selecting a link to patient medical history from a communication thread), due to a preconfigured dashboard setting, or other suitable trigger. For example, as shown in FIG. 2, the predictive VHA issued an alert at 5:00 PM that included reference to patient blood pressure in the form of a link. When the link is selected (e.g., via cursor 204), the dashboard 300 may be displayed showing the first graph 312 of the patient's blood pressure trend.

As explained earlier, one or more of the virtual healthcare assistants may be configured to monitor patient vital signs, via the output from the monitoring devices, the information stored in the digital twin, or other source. If a vital sign (or other health parameter) meets a predetermined condition, the one or more virtual healthcare assistants may be configured to output an alert to notify the one or more care providers attending the patient that patient follow-up may be needed. The alerts may be included in the communication thread, as discussed above. Additionally or alternatively, the alerts may be displayed on the dashboard. As shown, first graph 312 includes two alerts, each alert issued when mean arterial blood pressure dropped below a threshold, such as 80 mmHg. Selection of an alert may trigger display of a portion of the communication thread occurring on the communication channel where the alert was referenced.

Thus, as shown in FIG. 4, in response to user input selecting the second alert displayed on the dashboard 300 (e.g., the "alert 2" box) via cursor 204, a portion 402 of the communication thread 202 shown in FIG. 2 is displayed over dashboard 300. The portion 402 displayed may include only the portion of the communication thread that references the medical information that triggered the alert, and may also include additional messages around the message referencing the alert, in order to place the alert in context. In this way, a user may be able to quickly determine what else may have occurred around the time the alert was issued, determine if attending care providers administered treatment, or determine other relevant information. The portion 402 may not include the most recent messages in the communication thread, in some examples. Further, a user may not have access to the full communication thread when viewing the portion, and may not be able to interact (e.g., send messages) with the communication channel. Thus, a different selection on the dashboard may enable a user to view the full communication thread.

Additionally or alternatively, when viewing the portion of the communication thread, the user may scroll to view other portions of the communication thread or may enter another input to the portion of the communication thread to enable viewing of the full version of the communication thread. Alternatively, instead of showing a snippet from the communication channel, the full version of the communication thread may be displayed, with the focus point being the point in the communication channel that references the alert (which may enable the user to look before and after that point of the thread if desired). In another example, only the snippet of the communication thread may be displayed and if the snippet is selected, the full version of the communication thread may be displayed. In this way, either automatically or upon a further user input, the use may be able to interact with the communication thread (e.g., send a message via the communication thread).

Thus, the collaborative healthcare system shown in FIG. 1 may generate communication channel-dashboard pairs for each patient associated with the collaborative healthcare system. The collaborative healthcare system may include one or more computing devices, such as the care provider device 134. The computing device may include a display screen, and the computing device may be configured to display on the screen a dashboard. The dashboard may include patient medical information. The computing device may additionally be configured to display on the screen an alert related to the patient medical information. For example, as shown in FIG. 3, dashboard 300 may be displayed on a screen of a computing device (e.g., display device 202, which may be a screen of a computing device such as care provider device 134). Dashboard 300 may display patient medical information, such as the graph of the blood pressure trend of the patient (e.g., first graph 312). The displayed medical information may include an alert, such as alert 2 shown on first graph 312.

The alert may be selectable to launch a communication thread between a care provider and a virtual healthcare assistant. For example, as shown in FIG. 4, selection of alert 2 launches a communication thread between a care provider (Dr. Smith) and a virtual healthcare assistant (the predictive VHA). The selection of the alert enables a portion of the communication thread that references the displayed patient medical information to be seen within the communication thread. For example, FIG. 4 shows that in response to selection of alert 2, a portion 402 of the communication thread 202 (shown in FIG. 2) is displayed. The portion 402 includes reference to patient blood pressure, which is also displayed on the patient dashboard. Further, the alert may be displayed on the dashboard (at least initially) while the communication thread is in an un-launched state. For example, the alert may be displayed on dashboard 300 without display of the communication thread, e.g., while the communication thread is un-launched. In some examples, the full communication thread may be displayed rather than just a portion, with the full communication thread focused at the portion that references the patient blood pressure. According to some embodiments, the communication thread and the dashboard may both be displayed simultaneously on the display device.

In this way, the computing device provides a specific manner of displaying a limited set of information (e.g., the portion of the communication thread that specifically references medical information displayed on the dashboard) to the user, rather than using conventional user interface methods to display a generic index/list on a computer that may require the user to step through multiple menus and/or lists of communications and alerts to find the relevant portion of communication regarding the medical information. The dashboard interface-communication thread link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed dashboard interface-communication thread link may improve the efficiency of using the computing device by bringing together the portion of the communication thread most relevant to the user (as it relates to the displayed medical information) and the dashboard actually displaying the medical information, allowing the user to view the most relevant information on the communication thread without actually opening up the communication thread. The speed of a user's navigation through various views and windows may be improved because the disclosed link between the dashboard and the communication thread saves the user from navigating to the communication thread from the dashboard, opening the communication thread up, and then navigating within the communication thread to enable the portion of interest to be seen or a function of interest to be activated.

FIG. 5 shows a full version 502 of the communication thread that may be displayed in response to user input at the control button 308 (shown by cursor 204). The full version 502 may include the most recent messages sent on the communication channel. For example, full version 502 includes messages not shown in the portion 402 of the communication thread, such as the guideline VHA sending a message at 7:00 PM regarding patient glucose levels. Further, a user interface user input block is present at the bottom of the communication thread, via which a user may type a message to be sent on the communication channel. Due to space constraints, not all messages on the full version of the communication thread may be visible at one time, and thus the full version 502 may include a prompt where the user may swipe or enter other input to view additional messages. Additionally, while FIG. 5 shows the full version 502 superimposed over the dashboard 300, it is to be understood that in other examples, the dashboard may be replaced by the communication thread on the display device.

FIG. 6 shows an example where the full version 502 of the communication thread is displayed on display device 202 as a separate interface, without the dashboard also being displayed. In the example shown in FIG. 6, a user input to a link on the communication thread ("systolic BP is less than 100 mmHg") may trigger display of a preview 600 of patient blood pressure. As shown, preview 600 may include the first graph 312 of patient blood pressure over time, including the two alerts discussed previously. The preview 600 may be displayed in response to a single click or mouse hover over the link, for example.

Thus, the collaborative healthcare system shown in FIG. 1 may generate communication thread-dashboard pairs for each patient associated with the collaborative healthcare system. The collaborative healthcare system may include one or more computing devices, such as the care provider device 134. The computing device may include a display screen, and the computing device may be configured to display on the screen a communication thread. The computing device may additionally be configured to display on the screen a dashboard that can be reached directly from the communication thread. For example, as shown in FIG. 2, the communication thread may include a link that when selected launches a dashboard, such as the dashboard 300 shown in FIG. 3.

The communication thread displays communication between a care provider and a virtual healthcare assistant, and the communication thread includes medical information of a patient. At least a portion of the displayed medical information is selectable to launch the dashboard and enable the selected medical information to be seen within the dashboard. For example, referring to FIG. 2, the communication thread includes a link referencing patient medical information (herein, patient blood pressure), and selection of the link launches some or all of the dashboard. The dashboard includes display of the patient medical information included in the link (e.g., a trend of patient blood pressure). In an example, selection of the link may launch a full version of the dashboard, as shown in FIG. 2. In another example, selection of the link may launch only a portion of the dashboard, such as the preview shown in FIG. 6. The communication thread may be displayed while the dashboard is in an un-launched state, at least initially. For example, FIG. 2 shows the communication thread being displayed without display of the dashboard, and thus the dashboard may be unlaunched until the link the communication thread is selected.

In this way, the computing device provides a specific manner of displaying a limited set of information (e.g., the dashboard that specifically includes medical information referenced in the communication thread) to the user, rather than using conventional user interface methods to display a generic index/list on a computer that may require the user to step through multiple menus and/or lists of communications and alerts to find the relevant medical information. The communication thread-dashboard interface link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed communication thread-dashboard interface link may improve the efficiency of using the computing device by bringing together the medical information most relevant to the user (via the dashboard) and the communication thread referencing the medical information, allowing the user to view the most relevant medical information discussed on the communication thread without actually accessing an electronic medical record or separate interface where patient monitoring data may be displayed. The speed of a user's navigation through various views and windows may be improved because the disclosed link between the communication thread and dashboard saves the user from navigating to an electronic medical record database, opening the database up, and then navigating within the database to enable the medical information of interest to be seen or a function of interest to be activated.

FIG. 7 is a flow chart illustrating a method 700 for a collaborative healthcare system serving a medical facility, such as a hospital. Method 700 may be executed by a processor of a computing device (such as processor(s) 132 of server system 102 of FIG. 1) according to instructions stored on a non-transitory memory of the device (e.g., memory 130 shown in FIG. 1) in combination with the various signals received at the server system from components of the collaborative healthcare system (e.g., patient medical data signals from monitoring devices 120, communication from hospital operational systems 118, etc.) and signals sent from the server system to the care provider devices and/or other system components.

At 702, method 700 includes receiving a notification that a patient has been admitted to the medical facility. The notification may be received from the hospital operational systems, and may include a patient identifier, patient state (e.g., the condition for which the patient is being admitted), and care provider information. The care provider information may include identifiers of various care providers (such as doctors and nurses) that are currently attending to the patient.

At 704, method 700 includes generating a communication channel including a communication thread and a dashboard for the patient. In order to generate the communication channel, verified care providers of the patient (e.g., as indicated by the notification from the hospital operational systems) and one or more virtual healthcare assistants (VHAs) may be joined to the communication channel, as indicated at 706. The communication channel may facilitate text and/or rich-media based messages to be sent among all the verified care providers and VHAs that are joined to the communication channel. The one or more VHAs may include an EMR VHA, a guideline VHA, a predictive VHA, a listening VHA, a monitoring VHA, and/or other VHAs. To join the channel, each VHA may receive a message that a new channel has been opened and the access application (e.g., executing on the server system 102) may add the VHAs to the eligible participants of the channel. Moreover, in some examples, not all available VHAs may be invited to all channels (e.g., a sepsis VHA may not be invited in a non-relevant case or the listening VHA may not be invited due to patient refusal to be monitored by recording).

Generating the dashboard may include configuring the dashboard based on the patient state and/or user settings, as indicated at 708. As explained previously, a patient dashboard may be a graphical user interface that facilitates display of patient medical information, such as real-time vital signs, medical history, treatment plan, and/or other information. The dashboard may also include relevant/desired messages from the communication thread. Which medical information to display on the dashboard and in what format may be determined based on the patient state (e.g., current medical condition for which the patient is being treated) and/or on user settings, which may be configured by the end-viewer of the dashboard. In this manner, different patients may have different medical information displayed on different dashboards, and different care providers may view different medical information for the same patient, if desired.

At 710, method 700 includes receiving text- and/or rich-media-based messages from the participants on the communication channel, including care providers and VHAs. During the course of patient care, care providers may communicate with each other on the communication channel via messages of the communication thread to coordinate care, give care instructions, and/or confirm appropriate care is being carried out. Further, care providers may send requests to the VHAs via the communication thread for various information related to the patient care, including patient medical history, care guidelines, predicted future patient state, etc. Further still, VHAs may send notifications via the communication thread of changes in patient state, patient medical history, patient care guidelines, predicted future patient states, etc. The messages sent from a care provider may be sent from a care provider device (e.g., device 134) and received at the server system via a suitable connection (e.g., wired or wireless, such as via the Internet). The messages sent from the VHAs may be generated by the VHAs, which may be stored and executed on the server system, the cloud, and/or a remote device. As used herein, messages may refer to any suitable information sent and received on the communication thread, including but not limited to text messages (entered via typing, touch, or stylus input, voice input, or automatically generated by a VHA), images, voice messages (e.g., recordings of voice input), and videos.

At 712, method 700 includes distributing the received messages to other participants on the communication channel and saving the received messages as a communication thread. Each message that is sent to the server system may be tagged with various identifiers that identify the sender as well as the patient communication thread to which the message pertains (e.g., the patient identifier). The server system may then send the message to other participants of the communication channel, e.g., the care providers and/or VHAs that did not send the original message, and save the message as part of a saved communication thread. The saved communication thread may then be viewed by other users at other times, retrieved in response to a user request to view some or all of the communication thread, etc. However, in some examples, the device from which the original message was sent (e.g., the care provider device) may send the message to all other participants on the communication channel, and thus the server system may not distribute the message to the other participants.

At 714, method 700 includes receiving patient medical information. The patient medical information may be received from one or more patient monitoring devices that are configured to measure patient state and condition, including sensors that measure vital signs (e.g., blood pressure, heart rate, and blood oxygen level), diagnostic imaging modalities, microphones in proximity to the patient, and so forth. Additionally, the patient medical information may be received from the communication thread. For example, two care providers may be messaging each other on the communication thread and exchanging information relating to the patient, such as visual information (e.g., skin pallor, redness, or yellowness) of the patient that may be indicative of patient state. One or more of the VHAs may be configured to parse the message and determine that relevant medical information is being exchanged and then save the medical information as messages within the communication thread.

At 716, method 700 includes updating a digital twin of the patient with the medical information. The digital twin may be a digital replica/representation of the patient that is saved at the computing device (e.g., digital twin 108 saved on the server system 102). The digital twin may include patient demographic information, medical history, and other information to provide, to the extent possible, a simulation/representation of the current patient medical state. When new or updated medical information is received, the digital twin may be updated to reflect the most recent patient medical state. The digital twin may be accessed (e.g., by one or more of the VHAs) to retrieve patient medical information, predict future patient states (e.g., simulations may be performed using the information stored in the digital twin to determine the probability of the patient developing a certain condition), and provide appropriate context when retrieving care guidelines.

At 718, method 700 includes outputting the communication thread for display when prompted. In an example, the prompt may include an explicit request to view the communication thread for the patient, entered by selection of an appropriate link/control button on the patient dashboard or selection of the patient's communication thread from a collaborative interface, as indicated at 720. For example, as shown in FIG. 5, a message button may be displayed via the patient dashboard, and selection of the message button may trigger display of the communication thread for that patient. In another example, as shown in FIG. 10, a patient link may be selected to launch the communication thread from a collaborative system interface. In an example, the communication thread may be output for display automatically in response to a request from one or more of the VHAs, as indicated at 722. For example, a listening VHA may detect that one or more care providers are discussing a particular piece of the patient's medical history, and the listening VHA may send a portion of the communication thread that includes reference to the particular piece of medical history to the care provider's device for display. In another example, a VHA may detect that a patient vital sign has reached a level that may indicate a potential urgent patient condition and the VHA may output an alert regarding the vital sign on the communication channel. In some examples, issue of such an alert may prompt automatic display of the communication thread on each participant's display device.

At 724, method 700 includes outputting the dashboard for display when prompted. In an example, the prompt may include an explicit request to view the dashboard for the patient, entered by selection of an appropriate link/control button on the communication thread or selection of the patient's dashboard from a collaborative interface, as indicated at 726. For example, as shown in FIG. 2, a link to the dashboard may be displayed in the communication thread, and selecting the link may trigger display of the dashboard for that patient. In an example, the dashboard may be output for display automatically in response to a request from one or more of the VHAs, as indicated at 728. For example, the listening VHA may detect that a care provider is discussing the patient's current medical state and may automatically output the dashboard for display on the care provider's device so that the care provider may view patient medical information displayed in the dashboard that relates to the current medical state being discussed. Method 700 then returns.

FIG. 8 is a flow chart illustrating a method 800 for sending medical information to a care provider via one or more virtual healthcare assistants. Method 800 may be executed by a processor of a computing device (such as processor(s) 132 of server system 102 of FIG. 1) according to instructions stored on a non-transitory memory of the device (e.g., memory 130 shown in FIG. 1). As explained above with respect to FIG. 1, the server system 102 may store/execute one or more virtual healthcare assistants (VHAs) that are configured to perform certain tasks related to providing medical information of the patient to the one or more care providers attending to the patient, as explained below.

At 802, method 800 includes receiving a message from a care provider that includes a request for medical information relating to a patient. For example, as explained previously, each patient may have a dedicated communication channel including a communication thread that facilitates communication among the care providers treating the patient and one or more VHAs. When a care provider sends a message on the communication thread, the message may be received at the server system and the message may be analyzed to determine which patient the care provider is referring to and what information is being requested. The information request may be an explicit request, as indicated at 804, where the care provider explicitly asks for certain medical information, such as "please send me the patient's heart rate over the last four hours." In other examples, the request may be implicit, as indicated at 806. Implicit requests may include assumptions (on the part of the VHAs executing on the server system) that certain medical information may be helpful, such as when a change in patient vital signs is detected, that are not accompanied by an actual request by the care provider.

At 808, method 800 includes determining the appropriate VHA for handing the request for the medical information. For example, if the request includes a request for patient medical history, the EMR VHA may handle the request. If the request includes a request for patient care guidelines, the guideline VHA may handle the request. In some examples, each VHA may process a received message to understand (in natural language) the intent of the message and determine if the intent of the message includes a task that the VHA is trained/configured to perform. In some examples, the server system may include a central entity configured to understand the intent of the message (e.g., from the natural language of the message) and determine which VHA is best configured to handle the request. Then, the mapping from intent (and VHAs) to a specific API of a specific VHA is one-to-one, that is, only one VHA handles a specific intent (or intent-entity combination).

At 810, method 800 includes retrieving, with the selected VHA, the requested information. The requested information may be retrieved from the patient's EMR, as indicated at 812, or from the digital twin of the patient. In other examples, the requested information may be retrieved from a guideline service or predictive service, as indicated at 814. In still further examples, the requested information may be retrieved from the one or more monitoring devices that are currently monitoring the patient. At 816, method 800 includes sending a message including the retrieved medical information to the care provider via the communication channel. Method 800 then returns.

Figure 9:
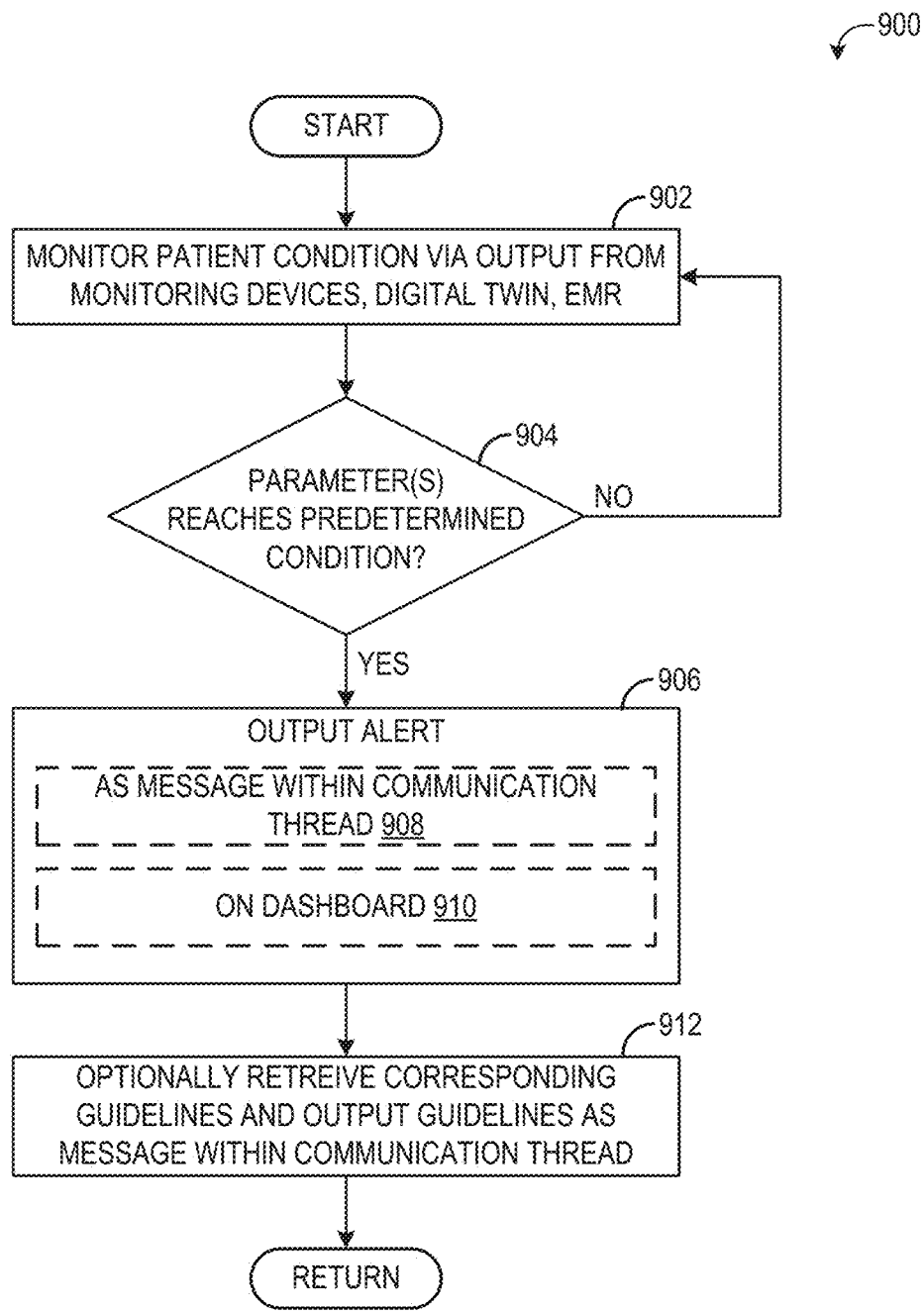

FIG. 9 is a flow chart illustrating a method 900 for monitoring a patient state via one or more virtual healthcare assistants. Method 900 may be executed by a processor of a computing device (such as processor(s) 132 of server system 102 of FIG. 1) according to instructions stored on a non-transitory memory of the device (e.g., memory 130 shown in FIG. 1). As explained above with respect to FIG. 1, the server system 102 may store/execute one or more virtual healthcare assistants (VHAs) that are configured to perform certain tasks related to monitoring a state or condition of the patient and notifying the care providers of the patient state, should the state change, as explained below.

At 902, method 900 includes monitoring the patient condition via output from one or more monitoring devices monitoring the patient (e.g., monitoring devices 120), a digital twin of the patient (e.g., digital twin 108), and/or an electronic medical record of the patient. As explained previously, one or more of the VHAs, such as the monitoring VHA, predictive VHA, and/or guideline VHA, may receive medical data regarding the patient's state in order to determine if the patient condition has changed, predict future patient events, etc. At 904, method 900 includes determining if one or more parameters of the patient condition has reached a predetermined condition. The one or more parameters may include vital signs or other health parameters that are currently being monitored, and the one or more parameters reaching the predetermined condition may include the one or more parameters reaching an abnormal condition, e.g., a condition that may indicate potential urgent patient conditions that necessitate treatment or evaluation from a care provider. For example, a parameter may include heart rate, and the heart rate reaching a predetermined condition may include the heart rate reaching a threshold, such as the heart rate dropping below a threshold heart rate. The abnormal condition (e.g., the threshold heart rate) may be based on a baseline condition for that patient. In the example of the heart rate, the patient may have a baseline heart rate of 75 bpm, which may represent an average of a plurality of heart rates of the patient measured over time while the patient is at rest. The threshold heart rate may be based on the baseline heart rate, such as equal to the baseline heart rate or a degree lower than the baseline heart rate (e.g., 75% of the baseline).

Other parameters that may be monitored include respiration rate, blood oxygen saturation, blood glucose, patient mental state, and so forth. Reaching the condition may include reaching a condition relative to a threshold, such as dropping below the threshold (as explained above with respect to the heart rate), exceeding the threshold (for example, a glucose level that exceeds a threshold may be indicative of an urgent condition), or other condition relative to a threshold. In still further examples, rather than monitor the value of a given parameter relative to a fixed threshold, method 900 may include detecting if a parameter has changed (e.g., by a threshold amount such as increased or decreased by 10% or more). Further, method 900 may include detecting if a set of parameters has changed in a specific manner, or may include determining if one or more parameters are indicative of a potential health issue. For example, the predictive VHA may be configured to enter a set of parameters (e.g., obtained by the monitoring VHA) into an external prediction service to determine if the parameters are indicative of a yet-undiagnosed or untreated medical condition.

If none of the parameters reaches a predetermined (e.g., abnormal) condition, method 900 returns to 902 and continues to monitor the patient condition. If one or more of the parameters does reach a predetermined condition, method 900 proceeds to 906 to output an alert referencing the one or more parameters. The alert may be output as a message within the communication thread on the communication channel for that patient, as indicated at 908. For example, as shown in FIG. 2, one of the VHAs (the predictive VHA) sent an alert on the communication thread for Patient ID 1234 at 4:00 PM indicating a deterioration in vitals was detected; another set of alerts was sent at 5:00 PM from the predictive VHA indicating suspected sepsis due to low blood pressure and a low Glasgow coma scale score. Additionally or alternatively, the alert may be output on the dashboard for the patient, as indicated at 910. For example, as shown in FIG. 3, two alerts are displayed on the blood pressure trend graph displayed within dashboard 300.

In some examples, in order to trigger an alert, only one parameter may need to reach its condition relative to its threshold. For example, a large drop in heart rate may trigger an alert regardless of the state of other parameters. In other examples, two or more parameters may need to reach respective conditions relative to respective thresholds to trigger an alert. For example, a small drop in heart rate coupled with a drop in blood oxygen saturation may trigger an alert, while only the small drop in heart rate alone may not trigger an alert. As such, a given parameter (e.g., heart rate) may actually be associated with multiple thresholds, such that dropping below a first threshold (e.g., 75% of the baseline heart rate) may trigger an alert while dropping below a second threshold (e.g., 90% of baseline heart rate) and not the first threshold may not trigger an alert unless the drop below the second threshold is also accompanied by a particular change in another parameter (e.g., a decrease in the blood oxygen level).

At 912, method 900 optionally includes retrieving corresponding guidelines and outputting the guidelines as a message within the communication thread on the communication channel. For example, if the change in parameters detected at 904 indicates a possibility of sepsis (as determined by the predictive VHA, for example), guidelines for treating sepsis may be output along with the alert indicating the possibility of sepsis. Method 900 then returns.

The technical effect of generating communication channels including communication thread-dashboard pairs for each patient is to facilitate communication among care providers of the patient and allow virtual healthcare assistants to provide information retrieval and patient monitoring duties, thereby reducing care provider work load, increasing communication among care providers to avoid redundant or missed care of the patient, and allowing the communication occurring on the channel to be saved in a central location accessible by the care providers. By saving the communication on the channel, patient medical state, care decisions, and more may be viewable at a later time in context. The saved communication on the communication channel may be used to auto-populate medical records, reports, or other forms, and may be available for larger-scale (e.g., hospital-wide) analytics on treatment guidelines and patient outcomes.

An example provides a system including a display and a computing device operably coupled to the display and storing instructions executable to: output, to the display, a patient-specific dashboard including medical information specific to the patient, the dashboard further including a displayed link to a patient-specific communication thread; and responsive to a user selecting the link, output to the display a portion of the communication thread, where the communication thread includes communication among one or more care providers monitoring the patient and one or more virtual healthcare assistants. In a first example of the system, the portion of the communication thread that is output to the display is a portion of the communication thread that references the medical information that is included on the dashboard. In a second example of the system, which optionally includes the first example, the one or more virtual healthcare assistants includes an electronic medical record (EMR) virtual healthcare assistant, and wherein the portion of the communication thread includes a first message including a request for the medical information from a care provider of the one or more care providers to the EMR virtual healthcare assistant and a second message including the medical information sent from the EMR virtual healthcare assistant, the EMR virtual healthcare assistant configured to retrieve the medical information from an EMR of the patient. In a sub-example of the second example, the display is a first display of a client computing device coupled to the computing device via a network, and the first message further includes a request to display the medical information on a second display, the second display coupled to the computing device via the network. For example, the first display may be a screen or a monitor of a care giver computing device and the second display may be a display present in an operating room or other room of the medical facility in which the patient and/or one or more care givers of the patient is located. The instructions on the computing device (e.g., the computing device may include the server system described above with respect to FIG. 1) are executable to output at least the second message for display on the second display in response to receiving the first message. In an example, the care giver operating the care giver computing device may enter an input in the form of a voice command ("trend the blood pressure over the last 12 hours and send it to the large screen in room 3") and the EMR VHA may determine (e.g., using natural language processing) the intent of the message, retrieve the blood pressure trend from the patient's EMR or other source (e.g., a digital twin of the patient stored on the server system), and output a graph illustrating the blood pressure trend to at least the second display. In some examples, the requested medical information may be output over the communication thread and as such any display currently viewing the communication thread may also display the requested medical information. If the requested display (e.g., the second display) is not currently displaying the communication thread, the communication thread may be launched on the requested display. In this way, a plurality of displays may be coupled to the computing device (e.g., the server system) via a network, and any one or more of the displays may be commanded to display requested information. In a third example of the system, which optionally includes one or both of the first and second examples, the one or more virtual healthcare assistants includes a predictive virtual healthcare assistant, and the portion of the communication thread includes a message sent by the predictive virtual healthcare assistant, the message including an alert notifying the one or more care providers that a parameter of the medical information has reached a predetermined condition. In some examples, the message including the alert notifying the one or more care providers that the parameter of the medical information has reached the predetermined condition may be sent by a monitoring virtual healthcare assistant rather than a predictive virtual healthcare assistant. In some examples, the parameter reaching the predetermined condition may include the parameter reaching a condition relative to a threshold, such as dropping below a threshold or increasing above a threshold. In a fourth example of the system, which optionally includes one or more or each of the first through third examples, the one or more virtual healthcare assistants includes a guideline virtual healthcare assistant, and wherein the portion of the communication thread includes a message sent by the guideline virtual healthcare assistant to the one or more care providers, the message including guidelines for treating or diagnosing a patient state associated with the parameter of the medical information. In a fifth example of the system, which optionally includes one or more or each of the first through fourth examples, the parameter of the medical information includes a quick sequential organ failure assessment (qSOFA) score, wherein the parameter of the medical information reaching the condition relative to the threshold includes the qSOFA score exceeding a threshold score, and wherein the guidelines include guidelines for diagnosing and/or treating sepsis based on the qSOFA score. In a sixth example of the system, which optionally includes one or more or each of the first through fifth examples, the portion of the communication thread includes a second link to the dashboard, and the instructions are further executable to, responsive to the user selecting the second link, output to the display the dashboard. In a seventh example of the system, which optionally includes one or more or each of the first through sixth examples, the one or more virtual healthcare assistants are configured to communicate on the communication thread using natural language and the communication among the one or more care providers and the one or more virtual healthcare assistants on the communication channel includes one or more of text-based communication, audio-based communication, image-based communication, and video-based communication. In an eighth example of the system, which optionally includes one or more or each of the first through seventh examples, the link is displayed within the medical information on the dashboard. In a ninth example of the system, which optionally includes one or more or each of the first through eighth examples, the link is a first link, wherein the dashboard further includes a second link, and wherein the instructions are executable to, responsive to the user selecting the second link, output to the display a full version of the communication thread.

An example provides a computing device comprising a display screen, the computing device being configured to display on the screen a dashboard including patient medical information, and additionally being configured to display on the screen an alert related to the patient medical information, wherein the alert is selectable to launch a communication thread between a care provider and a virtual healthcare assistant and enable a portion of the communication thread that references the displayed patient medical information to be seen within the communication thread, and wherein the alert is displayed while the communication thread is in an un-launched state. In a first example of the computing device, the virtual healthcare assistant is configured to obtain the patient medical information from one or more of an electronic medical record of the patient, a medical device monitoring the patient, and a digital twin of the patient. In a second example of the computing device, which optionally includes the first example, the virtual healthcare assistant is configured to output the alert to be included on the dashboard in response to detecting that a parameter of the patient medical information has reached a predetermined condition, such as reaching (e.g., exceeding or dropping below) a threshold. In a third example of the computing device, which optionally includes the first and/or second examples, the virtual healthcare assistant is further configured to output the alert to be included as a message of the communication thread, and wherein the message is included in the portion of the communication thread that references the patient medical information. In a fourth example of the computing device, which optionally includes one or more or each of the first through third examples, the patient medical information is obtained by the virtual healthcare assistant in response to a request from the care provider. In a fifth example of the computing device, which optionally includes one or more or each of the first through fourth examples, the virtual healthcare assistant is configured to output the alert to be included on the dashboard in response to a predicted condition of the patient determined by the virtual healthcare assistant from one or more of a digital twin of the patient, output from a medical device monitoring the patient, and an external prediction service. In a sixth example of the computing device, which optionally includes one or more or each of the first through fifth examples, the portion of the communication thread is launchable via a first selection to the dashboard and a full version of the communication thread is launchable via a second selection to the dashboard.

An example provides a computing device comprising a display screen, the computing device being configured to display on the screen a communication thread, and additionally being configured to display on the screen a dashboard that can be reached directly from the communication thread, wherein the communication thread displays communication between a care provider and a virtual healthcare assistant, the communication thread including medical information of a patient, at least a portion of the displayed medical information being selectable to launch the dashboard and enable the selected medical information to be seen within the dashboard, and wherein the communication thread is displayed while the dashboard is in an un-launched state. In a first example of the computing device, the communication thread includes one or more of a first message including a request for electronic medical record data of the patient from the care provider and a second message including the electronic medical record data of the patient from the virtual healthcare assistant, a third message including a request for guidelines related to the patient medical information from the care provider and a fourth message including the guidelines from the virtual healthcare assistant, and communication between multiple care providers. In a second example of the computing device, which optionally includes the first example, the portion of the displayed medical information that is selectable to launch the dashboard includes a link displayed within the displayed medical data. In a third example of the computing device, which optionally includes one or both of the first and second examples, the portion of the displayed medical information that is selectable to launch the dashboard includes a link on a displayed text communication from the virtual healthcare assistant.

An example provides a method including generating a plurality of patient-specific communication channels, wherein each communication channel comprises a patient-specific dashboard and a patient-specific communication thread. The method further includes, for a selected communication channel, storing text- and/or rich media-based messages between a care provider monitoring a patient and a virtual healthcare assistant on the communication thread of the selected communication channel, at least a portion of the messages on the communication thread including patient-specific medical data; and responsive to a prompt, outputting at least a portion of the communication thread that includes the patient-specific medical data to a display. In a first example of the method, the prompt includes user-selection of a link displayed in the dashboard of the selected communication channel. In a second example of the method, which optionally includes the first example, outputting at least the portion of the communication thread that includes the patient-specific medical data to the display includes outputting a first message from the care provider requesting the patient-specific medical data and a second message from the virtual healthcare assistant providing the requested patient-specific medical data.

Another example provides for a method including generating a plurality of patient-specific communication channels, wherein each channel comprises a patient-specific dashboard and a patient-specific communication thread. The method further includes, for a selected communication channel, outputting a least a portion of the communication thread of the selected communication channel to a display, the communication thread including communication between a care provider monitoring a patient and a virtual healthcare assistant; and responsive to a user-selection of a link displayed in the communication thread, outputting the dashboard of the selected communication channel to the display. In a first example of the method, the method further includes storing text- and/or rich media-based messages on the communication thread for the selected communication channel, a message on the communication thread including patient-specific medical data, and wherein the link displayed in the communication channel includes a link displayed within the patient-specific medical data. In a second example of the method, which optionally includes the first example, outputting the dashboard to the display includes outputting the dashboard including the patient-specific medical data.

In another representation, a method includes generating a patient-specific collaboration channel, comprising a patient-specific dashboard and a communication thread between a care provider monitoring the a patient and a virtual healthcare assistant; storing, at the channel, text- and/or rich media-based messages on the communication thread between the care provider and the virtual healthcare assistant, at least a portion of the messages on the communication thread including patient-specific medical data; and responsive to a prompt, outputting at least a portion of the communication thread that includes the patient-specific medical data to a display device. In an example, the prompt may be automatic (e.g., based on an alarm/detection of a condition from a virtual healthcare assistant running in the background). In an example, the prompt may include a manual interaction with the channel.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system for providing medical information comprising:
   a processor that, in response to executing machine-readable instructions, is to:
      generate a patient dashboard comprising the medical information for a patient and a patient communication thread;
      output the patient dashboard to a display, wherein the patient dashboard further comprises a first link proximate to a displayed parameter from the medical information, wherein the patient dashboard is displayed in response to a selection of a second link corresponding to the patient from a list of patients, and wherein, in response to a predefined selection of the first link, a preview is launched to display a portion of the patient communication thread corresponding to the displayed parameter, wherein the portion comprises a graph representing a trend of the displayed parameter, and wherein the preview remains in an unlaunched state until the predefined selection of the first link is provided;
      obtain a communication among one or more care providers monitoring the patient and one or more virtual healthcare assistants configured to communicate on the communication thread, the communication among the one or more care providers and the one or more virtual healthcare assistants on the communication thread comprising a text-based communication, an audio-based communication, an image-based communication, a video-based communication, or any combination thereof; and output the communication from the one or more care providers, the one or more virtual healthcare assistants, or any combination thereof, in the patient communication thread of the patient dashboard provided by the display.

2. The system of claim 1, wherein the one or more virtual healthcare assistants include an electronic medical record (EMR) virtual healthcare assistant, and wherein the communication thread comprises a first message including a request for the medical information from a care provider of the one or more care providers to the EMR virtual healthcare assistant and a second message including the medical information sent from the EMR virtual healthcare assistant, the EMR virtual healthcare assistant configured to retrieve the medical information from an EMR of the patient.

3. The system of claim 2, wherein the first message further comprises a request to display the medical information on a second display, the second display coupled to the system via a network, and wherein the machine-readable instructions are executable by the processor to output at least the second message for display on the second display in response to receiving the first message.

4. The system of claim 1, wherein the one or more virtual healthcare assistants comprises a predictive virtual healthcare assistant, and wherein the communication thread comprises a message sent by the predictive virtual healthcare assistant, the message comprising a notification indicating to the one or more care providers that the parameter of the medical information has reached a predetermined condition.

5. The system of claim 1, wherein the one or more virtual healthcare assistants comprises a guideline virtual healthcare assistant, and wherein the communication thread includes a message sent by the guideline virtual healthcare assistant to the one or more care providers, the message including guidelines for treating or diagnosing a patient state associated with the parameter of the medical information.

6. The system of claim 4, wherein the notification is selectable to launch a preview of a plot of the parameter of the medical information.

7. The system of claim 1, wherein the patient communication thread comprises a notification, wherein the notification indicates that the parameter exceeds a predetermined threshold.

8. The system of claim 6, wherein the notification provides a reminder indicating an action to be performed for a care protocol.

9. The system of claim 8, wherein the notification further comprises at least one of a patient state indicating a condition for which the patient is being admitted and care provider information.

10. A computing device comprising a display screen, the computing device being configured to display on the display screen a dashboard comprising patient medical information, and additionally being configured to display on the display screen a communication thread between a care provider and a virtual healthcare assistant, and an alert related to the patient medical information, wherein the alert is displayed while the communication thread is in an un-launched state, and wherein the virtual healthcare assistant is configured to obtain the patient medical information from an electronic medical record of the patient, a medical device monitoring the patient, a digital twin of the patient, or a combination thereof, and wherein the patient dashboard is displayed in response to a selection of a second link corresponding to the patient from a list of patients, and wherein, in response to a predefined selection of the first link, a preview is launched to display a portion of the patient communication thread corresponding to the displayed parameter, wherein the portion comprises a graph representing a trend of the displayed parameter, and wherein the preview remains in an unlaunched state until the predefined selection of the first link is provided.

11. The computing device of claim 10, wherein the virtual healthcare assistant is configured to output the alert to be included on the dashboard in response to detecting that a parameter of the patient medical information has reached a predetermined condition.

12. The computing device of claim 11, wherein the virtual healthcare assistant is further configured to output the alert to be included as a message of the communication thread, and wherein the message is included in a portion of the communication thread that references the patient medical information.

13. The computing device of claim 10, wherein the patient medical information is obtained by the virtual healthcare assistant in response to a request from the care provider.

14. The computing device of claim 10, wherein the virtual healthcare assistant is configured to output the alert to be included on the dashboard in response to a predicted condition of the patient determined by the virtual healthcare assistant from the digital twin of the patient, output from a medical device monitoring the patient, an external prediction service, or a combination thereof.

15. The computing device of claim 11, wherein the alert is selectable to launch a preview of a plot of the parameter of the medical information.

16. The computing device of claim 10, wherein the alert provides a reminder indicating an action to be performed for a care protocol.

17. The computing device of claim 10, wherein the alert further comprises at least one of a patient state indicating a condition for which the patient is being admitted and care provider information.

18. A method comprising:
generating a plurality of patient communication channels, wherein each communication channel comprises a patient dashboard and a patient communication thread; and for a selected communication channel,
storing messages between a care provider monitoring a patient and a virtual healthcare assistant on the communication thread of the selected communication channel, at least a portion of the messages on the communication thread including patient medical data; and in response to a user-selection of a link displayed within the patient dashboard, outputting at least a portion of the communication thread that comprises the patient medical data to the display, wherein the patient medical data included in the portion of the communication thread comprises at least one medical device data point from a plot of the medical device data of the patient, wherein the patient dashboard is displayed in response to a selection of a second link corresponding to the patient from a list of patients, and wherein, in response to the user-selection of the first link, a preview is launched to display the portion of the communication thread corresponding to the at least one medical device data point, and wherein the preview remains in an unlaunched state until the predefined selection of the first link is provided.

19. The method of claim 18, wherein the patient medical data included in the portion of the communication thread includes an indication, from the virtual healthcare assistant, that the patient is suspected to have a particular condition based on the at least one medical device data point.

20. The method of claim 19, wherein the plot of medical device data comprises a plot of blood pressure of the patient, wherein the particular condition is sepsis, and wherein the at least one medical device data point includes a blood pressure value of the patient indicative of sepsis.

* * * * *